US012465729B2

(12) United States Patent
Murphy

(10) Patent No.: US 12,465,729 B2
(45) Date of Patent: Nov. 11, 2025

(54) WIRE AND CATHETER PLACEMENT DEVICE

(71) Applicant: Main Circle Medical Inc., Charlotte, NC (US)

(72) Inventor: Kyle C. Murphy, Lexington, KY (US)

(73) Assignee: Main Circle Medical Inc., Charlotte, NC (US)

( * ) Notice: Subject to any disclaimer, the term of this patent is extended or adjusted under 35 U.S.C. 154(b) by 751 days.

(21) Appl. No.: 17/550,483

(22) Filed: Dec. 14, 2021

(65) Prior Publication Data

US 2022/0203075 A1 Jun. 30, 2022

Related U.S. Application Data

(60) Provisional application No. 63/215,493, filed on Jun. 27, 2021, provisional application No. 63/125,913, filed on Dec. 15, 2020.

(51) Int. Cl.
*A61M 25/09* (2006.01)

(52) U.S. Cl.
CPC .............................. *A61M 25/09041* (2013.01)

(58) Field of Classification Search
CPC .......... A61M 25/09041; A61M 25/065; A61M 2025/09116; A61M 5/32
See application file for complete search history.

(56) References Cited

U.S. PATENT DOCUMENTS

| | | | |
|---|---|---|---|
| 4,377,165 A | 3/1983 | Luther et al. | |
| 4,702,735 A | 10/1987 | Luther et al. | |
| 5,322,512 A | 6/1994 | Mohiuddin | |
| 5,415,177 A | 5/1995 | Zadini et al. | |
| 5,579,780 A * | 12/1996 | Zadini ............. | A61M 25/09041 604/168.01 |

(Continued)

FOREIGN PATENT DOCUMENTS

| | | |
|---|---|---|
| CN | 106823106 A | 6/2017 |
| EP | 2799021 A1 | 11/2014 |

(Continued)

OTHER PUBLICATIONS

European Patent Office; Search Report and Written Opinion in related International Patent Application No. PCT/US2021/063546 dated Apr. 26, 2022; 14 pages.

*Primary Examiner* — Yashita Sharma
*Assistant Examiner* — Lei Gonzalez
(74) *Attorney, Agent, or Firm* — Wood Herron & Evans LLP

(57) ABSTRACT

A device for interfacing with a syringe body and plunger for delivering a wire includes a needle configured for coupling with the syringe body having a bore for guiding a proximal end of the wire into the workspace. A slide is configured for coupling with the syringe plunger for moving with the syringe plunger between a forward position and a retracted position. The slide is releasably holds a distal end of the wire for advancing the proximal end of the wire forwardly in the needle when the slide moves the syringe plunger from the forward position to the retracted position. A wire advancing mechanism translates the movement of the wire distal end for advancing the proximal end of the wire forwardly as a result of the syringe plunger moving to the retracted position.

17 Claims, 24 Drawing Sheets

(56) References Cited

U.S. PATENT DOCUMENTS

| | | | | |
|---|---|---|---|---|
| 5,690,669 | A * | 11/1997 | Sauer .................... | A61M 29/02 606/192 |
| 6,197,001 | B1 | 3/2001 | Wilson et al. | |
| 6,217,558 | B1 | 4/2001 | Zadini et al. | |
| 6,371,944 | B1 * | 4/2002 | Liu ................. | A61M 25/09041 604/284 |
| 6,626,869 | B1 | 9/2003 | Bint | |
| 8,585,651 | B2 | 11/2013 | Asai | |
| 9,033,880 | B2 | 5/2015 | Sheldon et al. | |
| 9,420,992 | B2 | 8/2016 | Sheldon et al. | |
| 9,427,207 | B2 | 8/2016 | Sheldon et al. | |
| 9,439,653 | B2 | 9/2016 | Avneri et al. | |
| 9,616,201 | B2 | 4/2017 | Belson | |
| 9,861,739 | B2 | 1/2018 | Sheldon et al. | |
| 9,872,971 | B2 | 1/2018 | Blanchard | |
| 9,950,139 | B2 | 4/2018 | Blanchard et al. | |
| 9,956,382 | B2 * | 5/2018 | Hwang .............. | A61B 5/15003 |
| 9,999,440 | B2 | 6/2018 | Sheldon et al. | |
| 10,124,144 | B2 | 11/2018 | Avneri et al. | |
| 10,384,039 | B2 | 8/2019 | Ribelin et al. | |
| 10,898,689 | B2 | 1/2021 | Holt | |
| 10,898,690 | B2 | 1/2021 | Williams et al. | |
| 10,987,488 | B2 | 4/2021 | Avneri et al. | |
| 11,931,531 | B2 | 3/2024 | Scherich et al. | |
| 11,992,632 | B2 | 5/2024 | Burkholz et al. | |
| 12,023,454 | B2 | 7/2024 | Bursavich et al. | |
| 2006/0047246 | A1 | 3/2006 | Anders | |
| 2007/0088273 | A1 | 4/2007 | Rafi | |
| 2011/0152836 | A1 | 6/2011 | Riopelle et al. | |
| 2013/0178711 | A1 | 7/2013 | Avneri et al. | |
| 2014/0214005 | A1 * | 7/2014 | Belson .............. | A61M 25/0606 604/510 |
| 2015/0087970 | A1 | 3/2015 | Sheldon et al. | |
| 2015/0087992 | A1 | 3/2015 | Sheldon et al. | |
| 2015/0216556 | A1 | 8/2015 | Sheldon et al. | |
| 2018/0126126 | A1 * | 5/2018 | Ornelas Vargas ........................... | A61M 25/09041 |
| 2019/0046769 | A1 | 2/2019 | Avneri et al. | |
| 2019/0255294 | A1 | 8/2019 | Mitchell et al. | |
| 2020/0147349 | A1 | 5/2020 | Holt | |
| 2020/0197682 | A1 | 6/2020 | Franklin et al. | |
| 2021/0128882 | A1 | 5/2021 | Holt | |
| 2022/0218956 | A1 | 7/2022 | Harding et al. | |
| 2023/0099654 | A1 | 3/2023 | Blanchard et al. | |
| 2023/0218867 | A1 | 7/2023 | Howell et al. | |
| 2024/0198050 | A1 | 6/2024 | Bowman | |
| 2024/0207582 | A1 | 6/2024 | Chhikara et al. | |
| 2024/0342440 | A1 | 10/2024 | Horst et al. | |

FOREIGN PATENT DOCUMENTS

| | | | |
|---|---|---|---|
| FR | 2750608 | A1 | 1/1998 |
| WO | 9801178 | A1 | 1/1998 |
| WO | 2007024986 | A2 | 3/2007 |
| WO | 2015148478 | A1 | 10/2015 |
| WO | 2018136436 | A1 | 7/2018 |
| WO | 2019204731 | A1 | 10/2019 |
| WO | 2021150948 | A1 | 7/2021 |
| WO | 2023059704 | A1 | 4/2023 |
| WO | 2024097201 | A1 | 5/2024 |

* cited by examiner

WIRE AND CATHETER PLACEMENT DEVICE

CROSS-REFERENCE TO RELATED APPLICATIONS

This application claims the benefit of priority to U.S. Provisional Patent Application Ser. No. 63/125,913, filed Dec. 15, 2020, and U.S. Provisional Patent Application Ser. No. 63/215,493, filed Jun. 27, 2021, the disclosures of which are incorporated by reference herein in their entireties.

TECHNICAL FIELD OF THE INVENTION

The present invention is directed to a device for positioning a guide wire into tissue and particularly into a workspace in the tissue, such as vasculature, for the positioning of other elements for the performance of medical procedures.

BACKGROUND OF THE INVENTION

Commonly in medicine and surgery, it is necessary to position elements, such as catheters and other elements into workspaces within tissue, such as in vasculature. The Seldinger technique is often used for such positioning of a guide wire. Typically in such a technique, a needle is inserted into a vein, artery, or other body cavity or workspace. Frequently, a syringe is attached to the needle, and a user draws the syringe back to generate negative pressure as the needle is advanced into skin and tissue. While the needle goes through the skin and subcutaneous tissue, the lumen or bore of the needle is blocked and a user is only able to pull the plunger back a short distance due to the vacuum and negative pressure created within the syringe. Once the needle tip or bore enters the target space, such as the inside of a blood vessel, the syringe is filled with blood, air, or another fluid under the force of the negative pressure. A user inserting the needle is able to visualize this to know the needle is properly placed.

Once the needle tip is in the target space, the syringe is removed from the needle. From there, a flexible wire is passed through the needle into the target space. The needle then can be slid back and removed over the wire. A dilator, which is a firm piece of plastic, is passed over the wire into the tissue and workspace and then removed. A catheter, which is generally the same size as the dilator but more flexible, can then be placed into the target space over the wire, being guided by the wire.

One of the current drawbacks to the existing technique is that several issues can arise at the various stages, from the removal of the syringe from the needle to the feeding of the wire into the needle and into the workspace. For a user, moving and manipulating the wire can be awkward and difficult. The wire is thin and frequently flops around. As such, the wire can become nonsterile if part of it hits something outside of the sterile field. It can also be difficult to get the wire to go into the back of the needle. The needle can also move while the syringe is removed therefrom and while a user reaches for the wire and threads it into the needle. In such a scenario, the needle can either pull out of the target space so that the wire cannot be advanced. The needle might also be advanced further than desired. This may create complications. For example, in the case of an internal jugular central venous catheter placement, the carotid artery is often posterior. If the needle goes in further than desired in the vein, the needle tip can then be in an artery without the user knowing it. The wire is passed into the artery. The artery might then be dilated. This can lead to severe complications, given that a larger hole has just been made in a high-pressure arterial system.

Accordingly, there is a need for a device and method that can improve safety and time efficiency in the Seldinger technique and similar techniques for positioning a wire in a body workspace. There is also a need to improve ergonomics and allow a user to more easily draw negative pressure and receive feedback in the process during wire placement.

SUMMARY OF THE INVENTION

A device for interfacing with a syringe body and plunger for delivering a wire into a tissue workspace includes a needle configured for coupling with the syringe body and having at least one bore for guiding a proximal end of the wire into the workspace. A housing is configured for coupling with the syringe body and includes a portion for engagement by a user, such as one or more grip portions. A slide is configured for coupling with the syringe plunger for moving the syringe plunger between a forward position and a retracted position. The slide also includes a portion for engagement by a user for its movement. The user can grip the housing and slide for engaging and manipulating the syringe. The slide is releasably coupled with a distal end of the wire for moving the distal end and advancing the proximal end of the wire forwardly in the needle when the slide moves the syringe plunger from the forward position to the retracted position. For example, the slide may include a wire gripping structure for releasably gripping the distal end of the wire for moving the distal end of the wire when the syringe plunger is moved. For advancing the proximal end of the wire forwardly in the needle when the slide moves the syringe plunger to a retracted position, one embodiment includes a wire advancing mechanism for translating the movement of the wire distal end for advancing the proximal end of the wire forwardly in as a result of the syringe plunger moving to the retracted position.

DETAILED DESCRIPTION OF EMBODIMENTS OF THE INVENTION

Figure 1:
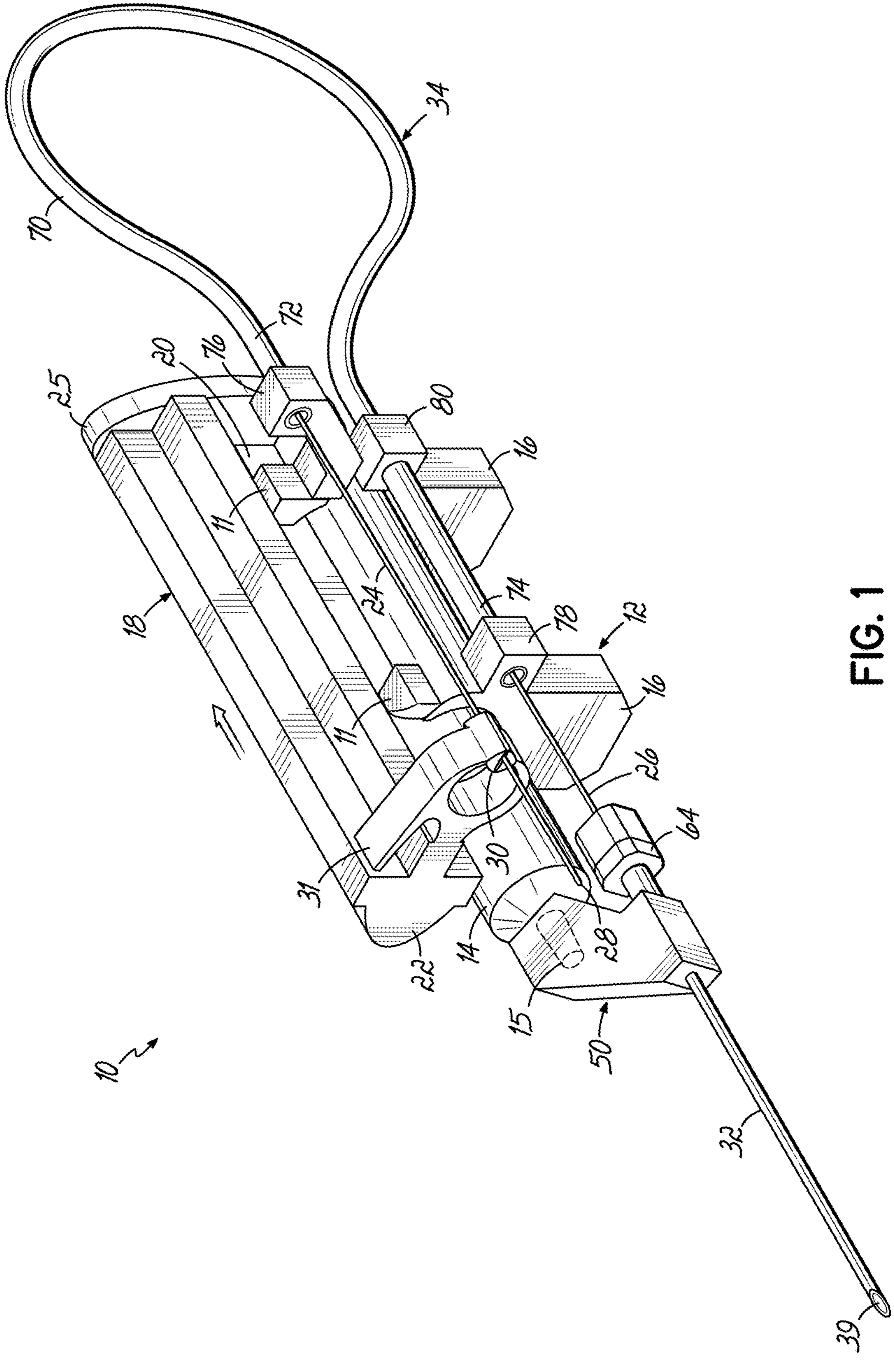
FIG. 1 is a perspective view of wire and catheter placement device in accordance with an embodiment of the invention.

FIG. 1 illustrates an embodiment of a device 10 for advancing a wire into a body space or workspace, such as the vasculature of an animal, such as a human. Such wire advancement can be used for a number of different medical procedures and is generally referred to as the Seldinger technique. Herein, the term vasculature will often be used to generically refer to a space or workspace in tissue in a body, but the use of the invention is not limited to just wire placement in vasculature. Furthermore, while the discussed embodiments are for placement of a guide wire to position other elements in the body workspace, other wire structures may be inserted with the device, and so the element is referred to herein as a "wire".

Figure 2A:
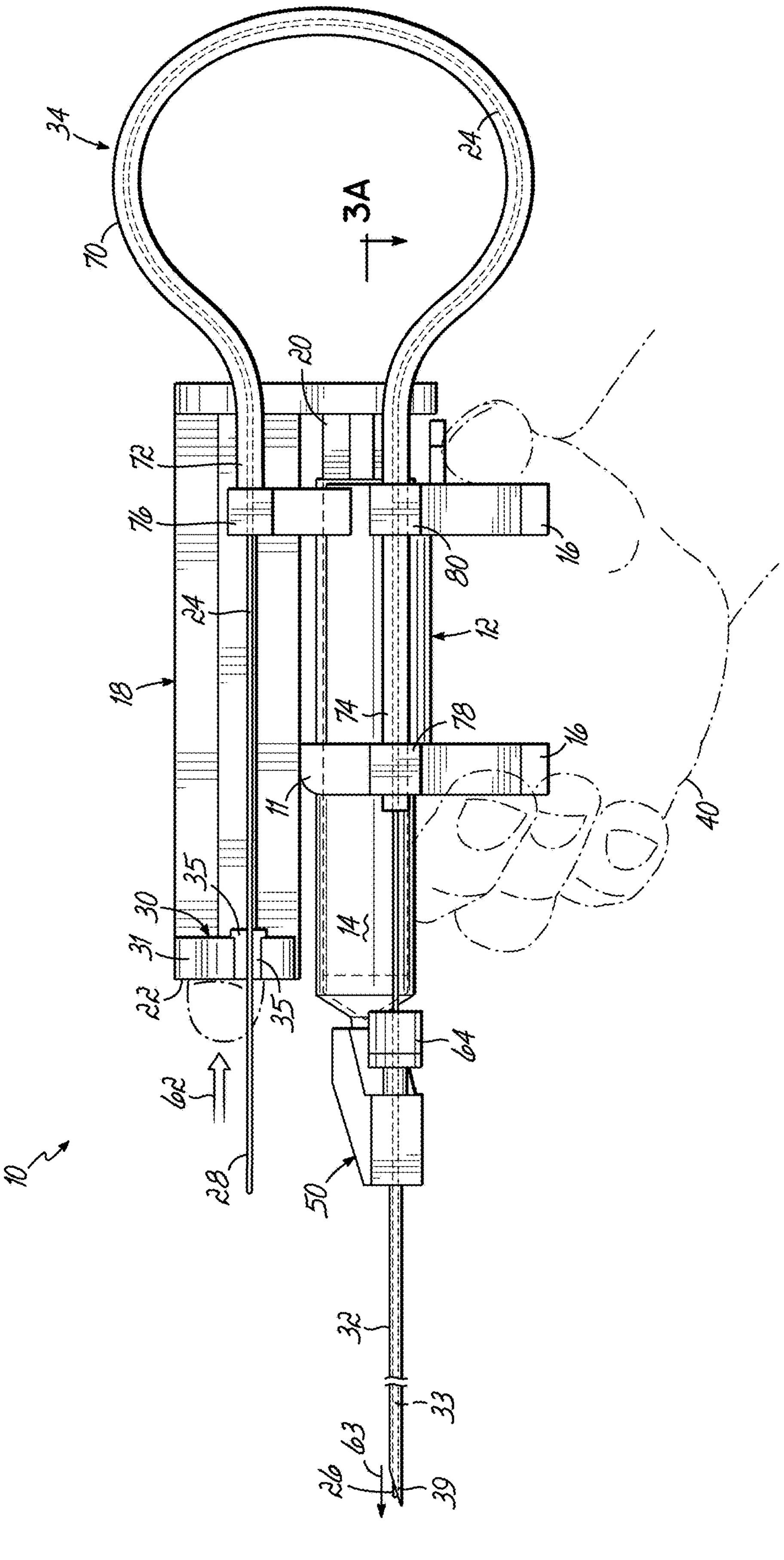
FIG. 2A is a side view of the wire and catheter placement device of FIG. 1, in a forward position, in accordance with an embodiment of the invention.
Figure 2B:
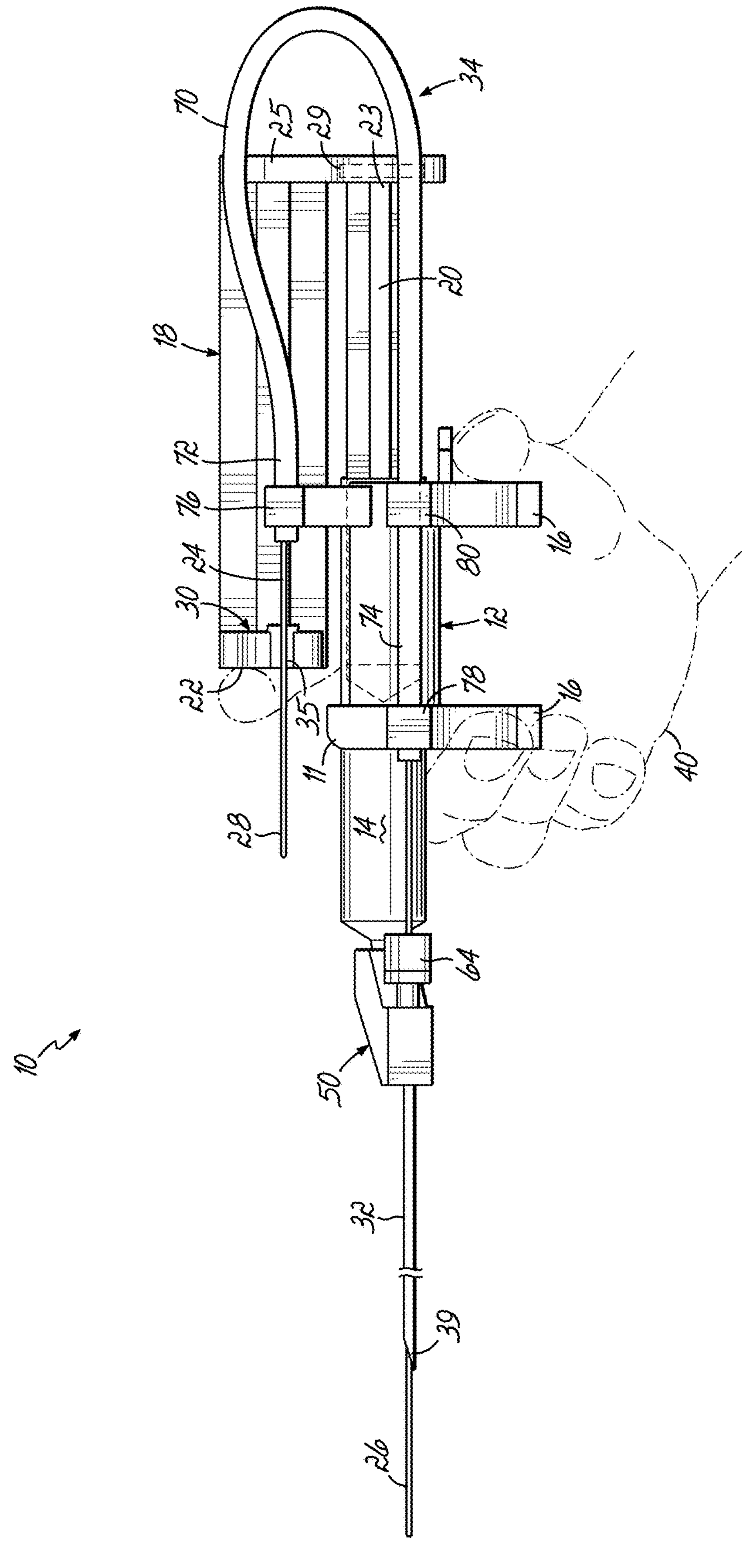
FIG. 2B is a side view of the wire and catheter placement device of FIG. 1, in a retracted position, in accordance with an embodiment of the invention.

Device 10 includes a housing 12 that includes or is configured for coupling with a syringe body 14. The housing defines a portion, such as one or more grip portions 16 for engagement by a user. The housing provides a way of gripping the syringe body. A slide element or slide 18 is positioned along the outside of the housing and is configured for coupling with a syringe plunger 20. The syringe plunger 20 moves inside the syringe body 14 between a forward position as illustrated in FIG. 2A, for example, and a retracted position as illustrated in FIG. 2B. The slide 18 also includes a grip portion 22 for engagement by a user to move the slide 18 and the syringe plunger 20 with respect to the housing 12 and syringe body 14. The slide acts as an extension of the plunger. Specifically, the slide 18 provides a way for a user to more easily engage and move the syringe plunger 20 from the forward position to the retracted position during the use of the device 10.

Device 10 manipulates and includes a wire 24 for delivery and placement into a tissue workspace. The wire 24 includes a proximal end 26 and a distal end 28. The slide is releasably coupled with a distal end of the wire for moving the distal end and thereby advancing the proximal end forwardly in the needle when the slide moves the plunger from a forward to a retracted position. The slide 18 in one embodiment as shown in FIG. 1 includes a wire gripping structure 30 that releasably engages or grips the distal end 28 of the wire for facilitating movement of the wire with the plunger as described herein. A needle 32 is coupled with the syringe body 14 and is also configured to have a bore for guiding the proximal end 26 of the wire into vasculature or another workspace in accordance with features of the invention. More specifically, movement of the slide 18 and coupled syringe plunger 20 rearwardly to a retracted position away from the needle 32 in the syringe body will draw negative pressure in the needle. The movement of the slide 18 that releasably grips the wire will also seek to advance the wire 24 through needle 32 into the vasculature. To that end, a wire advancing mechanism 34 is coupled generally between the slide 18 and housing 12 as seen in FIG. 1. The wire advancing mechanism 34 acts on the wire to translate movement in one direction into movement in another direction. The mechanism 34 is configured for translating the movement of the wire distal end into movement for advancing the proximal end 26 of the wire forwardly into and through needle 32 when the slide 18 moves the syringe plunger 20 from the forward position to a rearward or retracted position as illustrated in FIG. 2B.

The purpose of the wire advancing mechanism is to reverse or translate the rearward movement of the slide 18 and the accompanying movement of the syringe plunger 20 to the retracted position and create a forward movement of the proximal end of the wire 24 into and through the needle in one movement stroke. As illustrated in FIGS. 2A and 2B, a hand 40 of a human operator engages the respective grip portions 16 and 22 of the housing 12 and slide 18 and moves the slide toward a retracted position along the housing as illustrated in FIGS. 2A and 2B. The wire gripping structure 30 of the slide 18 in FIG. 1 releasably grips the distal end 28 of the wire so the slide and wire are coupled together. The movement of the slide 18 and syringe plunger 20 to a retracted position causes the distal end of the wire to move toward the wire advancing mechanism 34. The wire advancing mechanism 34 reverses or translates that rearward movement of the wire distal end into a forward or advancing movement of the wire proximal end 26 into and through the needle 32. As the slide 18 and plunger 20 are moved further to the retracted position, the proximal end 26 of the wire is advanced further forwardly through the needle, and ultimately into vasculature or another workspace into which the needle is inserted.

In that way, the device 10 of the present invention provides a single motion and unique and smooth forward movement of the wire through needle 32 and into the vasculature as the plunger is moved to the retracted position and a negative pressure is drawn and released with respect to the syringe plunger 20 moved by slide 18. The slide 18 is coupled with both the wire and plunger and moves both the syringe plunger 20 as well as wire 24 in a single stroke or movement of the slide 18 as described further herein.

Figure 3A:
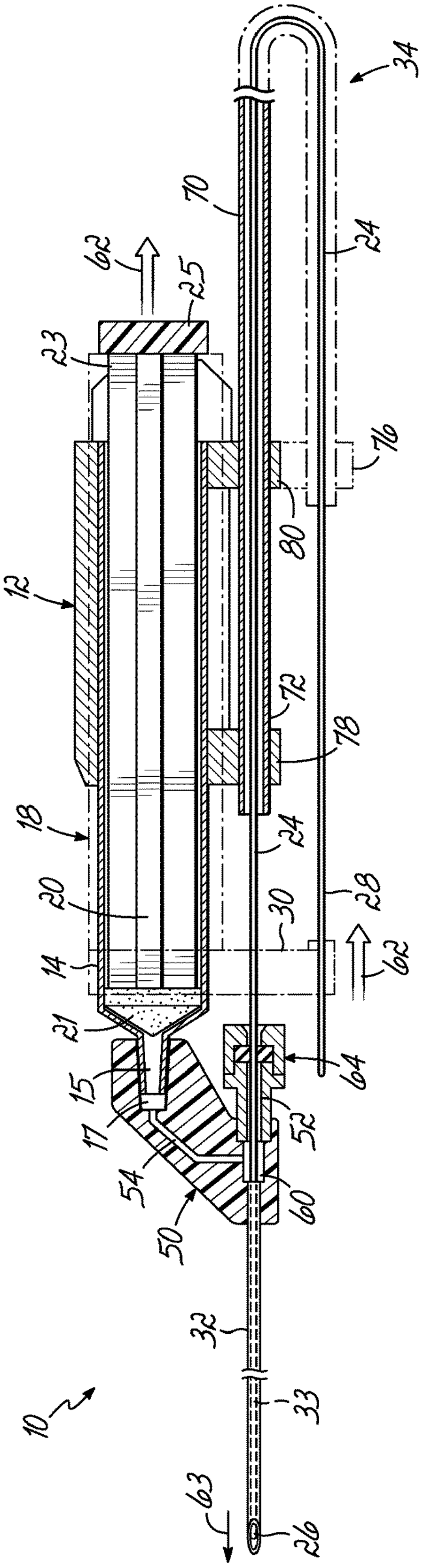
FIG. 3A is a top view, in partial cross-section, of the wire and catheter placement device of FIG. 1, in a forward position, in accordance with an embodiment of the invention.
Figure 3B:
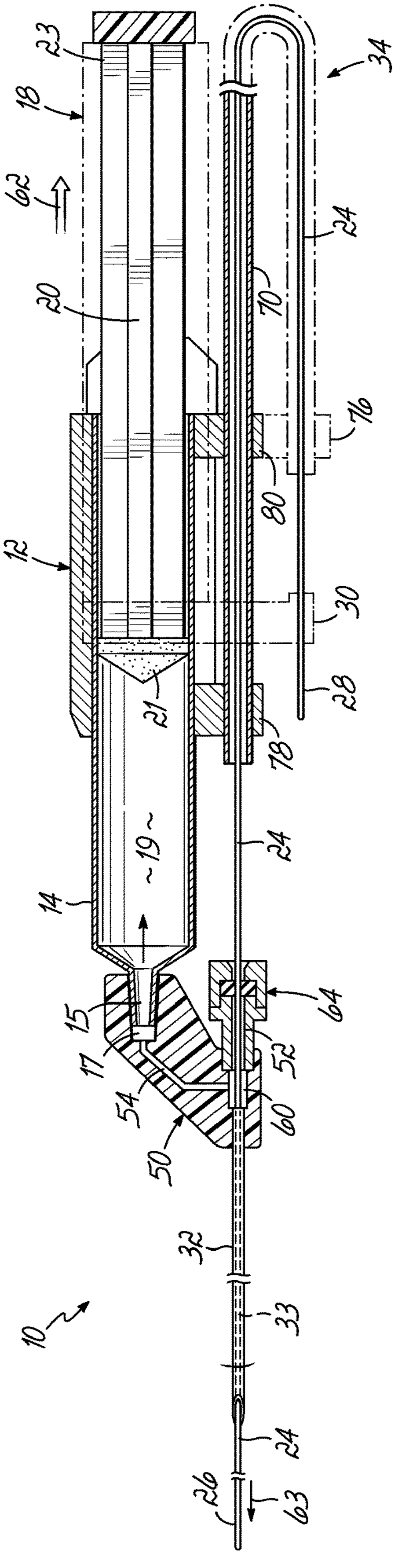
FIG. 3B is a top view, in partial cross-section, of the wire and catheter placement device of FIG. 1, in a retracted position, in accordance with an embodiment of the invention.

The needle 32 is configured for coupling with the syringe body and has at least one base or lumen for guiding a proximal end of the wire. Device 10 further includes a needle mount 50 for coupling the needle 32 with the device. The needle mount 50 couples the needle 32 with both the syringe body 14 as well as the wire 24. FIGS. 3A and 3B illustrate cross-sectional top views of the device with the slide and syringe plunger in the forward position and then the slide and syringe plunger in the retracted position used for advancing wire 24. The needle mount 50 includes a guide passage 52 coupled with needle bore 33 for directing movement of the wire 24 into and through the needle 32. The needle mount 50 also includes a vacuum passage 54 that is coupled with the syringe body 14 to create a negative pressure in the needle bore when the syringe plunger is moved to the retracted position as illustrated in FIG. 3B. As described herein, movement of the slide and the syringe plunger to the retracted position as shown in FIG. 3B will draw a negative pressure within the needle 32 through needle mount 50. As long as the needle is blocked by tissue, that negative pressure will generally prevent significant rearward movement of the slide and syringe plunger to the retracted position under the force of a gripping human hand on the respective grip portions 16 and 22 of the housing and slide. The slide and plunger may move slightly to create the negative pressure with hand pressure but will be prevented from moving readily to the full retracted position. Once the needle tip penetrates through the tissue and the vasculature and the negative pressure is broken, the slide and syringe plunger may be drawn or moved more easily in the device 10 to the retracted position. Simultaneously, the movement of the slide and plunger also moves the wire gripping structure 30 rearwardly with respect to needle 32. This pushes wire 24 through the wire advancing mechanism 34 and turns or reverses or translates the wire movement and then advances the proximal end 26 of the wire forwardly through needle 32 as illustrated in FIG. 3B.

In the embodiment of the invention illustrated in FIGS. 1-3B, the needle mount 50 creates an airtight passage in both the vacuum passage 54 as well as the guide passage 52. The needle 32 is hollow and includes the bore 33 that is dimensioned to allow for passage of wire 24 therethrough. The bore 33 is also dimensioned to allow the simultaneous passage of air and/or fluid through the needle 32 when the wire 24 moves within the needle. The needle mount 50 forms an intersection point 60 for the vacuum passage 54, the bore 33 of the needle, and the guide passage 52 for the wire 24. The syringe body 14 forms an airtight seal with needle mount 50 and passage 54. In one embodiment of the invention as illustrated in the figures, the syringe body 14 includes a tip 15 that fits in an appropriately formed opening or cavity 17 in the needle mount. The vacuum passage 54 through engagement with the intersection section 60 and needle bore 33 provides a connection between the needle 32 and the internal space 19 of the syringe body as illustrated in FIG. 3B. When the syringe plunger 20 is forced into the retracted position by a user as illustrated by arrows 62, pressure is created to draw gas or fluid in through needle 32, through the vacuum passage 54 and into the internal space 19 of the syringe body. In order to ensure that such a negative pressure is created in the needle 32 and particularly in the bore 33 of the needle, the passage 52 which guides wire 24 also has to be airtight in the embodiment of FIG. 1. To that end, the needle mount includes a sealing mechanism 64 that engages with guide passage 52 and wire 24 for providing the airtight seal in the guide passage. That is, the sealing mechanism 64 engages with wire 24 as it passes through the sealing mechanism and into the guide passage 52 so that negative pressure is maintained and wire 24 may move through the guide passage of the needle mount and through needle 32 at the same time that negative pressure is being drawn through movement of the plunger 20 within the syringe body 14. In one embodiment, the sealing mechanism 64 may entail a rubber or silicone element having a hole for passing the wire. The wire 24 could be a smooth wire or a coiled wire. A coiled wire may have a coating thereon or could have a substance applied, such as petroleum jelly, as a coating material.

In the present invention, using a needle mount 50 as shown separates the fluid/air passage of the syringe from the wire passage. This allows the syringe to be removed while the wire is still in the needle and provides the ability to perform a Fabian test while the wire is already positioned or advanced. This can verify that the wire is not in an artery rather than an intended vein.

Figure 14:
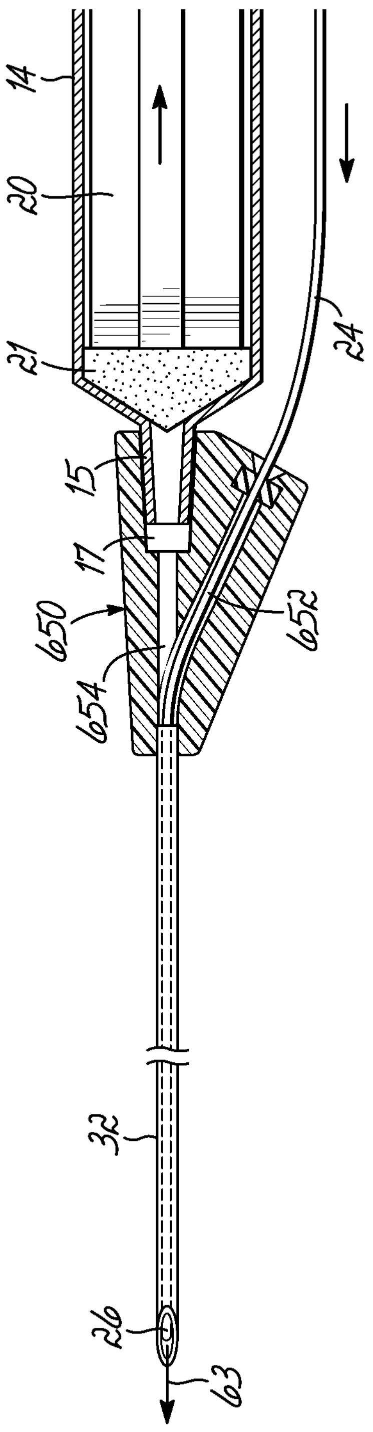
FIG. 14 is a top view of an alternative device of the invention.

The needle mount 50 has a syringe passage that is adjacent to but not inline with the needle. Rather the guide passage is inline with the needle to move the wire straight into the needle. This reduces friction and provides easier advancement. In another embodiment as shown in FIG. 14, the syringe or vacuum passage is aligned with the needle and the wire enters at an angle. A pre-manufactured needle may be used in the needle base. Alternatively, the needle may be manufactured directly with the needle base. In one embodiment, the needle base may be made of a clear material or include a clear area to more readily see when fluid enters the needle.

As may be appreciated, the syringe plunger 20 may be configured to resemble a typical syringe plunger having an elongated body portion which is terminated in a rubber or plastic stopper 21 that seals with the internal wall of the syringe body 14 and creates an air and fluid tight seal. A force provided in the direction of arrow 62 on the end 23 of the syringe plunger 20 will move the syringe plunger 20 and stopper 21 to a retracted position as illustrated in FIG. 3B. FIG. 3A shows the syringe plunger 20 and stopper 21 in the forward position against the end of the springe body 14 and proximate the tip 15. If the needle tip is blocked, negative pressure is created in the syringe.

In accordance with one aspect of the invention, the housing 12 is configured for coupling with the syringe body. In one embodiment, the syringe body 14 may be formed as a unitary structure with the housing wherein the syringe body includes the integrally molded housing and grip portions. In another embodiment of the invention, the housing 14 may be configured to receive a separate syringe body 14 with the syringe body in a proper position with respect to the grip portions 16 of the housing. Similarly, the slide 18 may be formed and configured for coupling with a syringe plunger or the slide may be formed together with or as an extension of a syringe plunger as a single piece, such that the slide and grip portions move as one piece with the syringe plunger. Alternatively, the slide 18 may be formed and configured to couple to a separate syringe plunger in order to couple the movement of one to the other. In that way, a housing 12 and slide 18 might be configured and dimensioned to receive and utilize a typical syringe having a syringe body and syringe plunger.

Figure 1A:
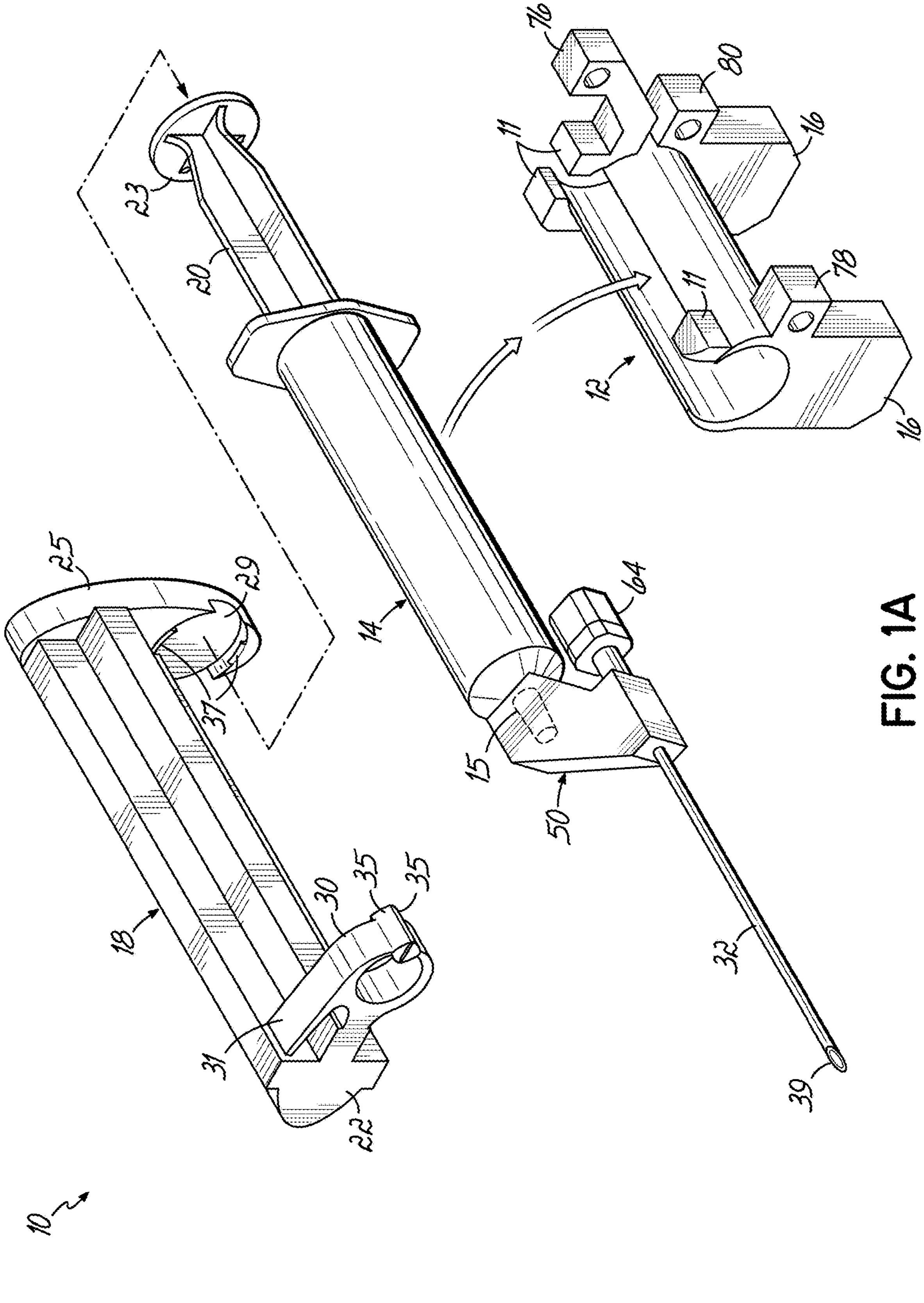
FIG. 1A is an exploded, perspective view of wire and catheter placement device in accordance with an embodiment of the invention.

To that end, FIG. 1A shows one embodiment of the device 10 wherein housing 12 includes a generally cylindrical passage 17 configured for receiving syringe body 14 to couple with the syringe body. The slide 18 is configured to slide on or adjacent to the housing 12 and is positioned generally parallel to the housing. Guide elements 11 on housing 12 may engage the slide 18 to ensure a straight movement of the slide to the retracted position with respect to the housing and the syringe body. Slide 18 has an end 25 that has an indent 29 or other structure for engaging an end 23 of a syringe plunger 20 to hold the end 23 and couple the slide and plunger. The plunger and slide engagement may be a friction fit or the plunger end 23 might be held in the indent by one or more tabs 37 that snap on the end 23. In that way, the slide acts as an extension of the plunger to move the plunger.

The housing 12, syringe body 14, slide 18, and syringe plunger 20 may be formed of a suitable material, such as a plastic material that is lightweight and may be sterilized. The material provides sufficient rigidity for movement of the plunger in the syringe body as well as gripping and guiding of the wire 24.

In accordance with one feature of the invention, the wire advancing mechanism 34 is configured for advancing the proximal end of the wire forwardly into and through the needle when the slide moves the syringe plunger from the forward position to the retracted position. That is, the wire advancing mechanism 34 is functional to translate or change the direction of the wire such that moving the syringe plunger rearwardly to a retracted position away from the needle actually simultaneously advances the wire forwardly into and through the needle and ultimately into vasculature into which the needle penetrates as described herein. This proceeds in one single and fluid motion wherein moving the plunger to the retracted position simultaneously advances the wire forwardly into the needle.

FIGS. 1-3B illustrate one wire advancing mechanism 34 in accordance with an embodiment of the invention that includes a loop guide 70 for reversing or translating the direction of the wire movement. The loop guide is generally positioned between the slide 18 and housing 12 so as to provide the reversal or translation in the direction of the wire movement with respect to the movement of the slide 18 and the syringe plunger. Specifically, referring to FIG. 1, the wire advancing mechanism 34 includes a loop guide 70 that has an input end or distal end 72 positioned to receive a wire from the wire gripping structure 30 of the slide 18 and an output end or proximal end 74 for guiding a proximal end of the wire 24 and outputting the wire into needle mount 50 and ultimately into needle 32. The loop guide 70 may be a closed tube as illustrated in FIG. 1. Alternatively, the loop guide might be open and form an appropriate structure for capturing wire 24 and guiding it from the distal end 72 to the proximal end 74. As illustrated in FIG. 1, the housing 12 may be appropriately formed to include mount sections 76, 78 that interface with and contain the respective distal end 72 and proximal end 74 of the loop guide 70. Depending upon the length of the housing, as well as the length of the loop guide 70 and the length of the syringe body, slide, and syringe plunger, one or more additional mount sections 80 may be implemented in the housing 12 for holding a portion of the loop guide 70 between the distal end 72 and proximal end 74. As illustrated in FIG. 2A, the wire 24 is contained by loop guide 70 which reverses direction of the movement of the wire 24 and slide 18 as illustrated by reference arrow 62 and changes the direction of movement of the proximal end 26 of the wire 24 in the direction of arrow 63. In that way, negative pressure or a vacuum may be drawn through syringe body 14 by movement of slide 18 and the plunger rearwardly in the direction of arrow 62 and simultaneously, when the pressure is released, the proximal end 26 of the wire will advance forwardly in the direction of arrow 63 or in the direction of the movement of needle 26 into the workspace as described herein.

The terms proximal and distal as used herein, particularly with respect to the wire 24 and its ends or sections are used to indicate one end proximate to the body which proceeds through the needle and into the workspace and the other end which is spaced from the needle and is gripped and pushed by movement of the slide 18 and the plunger. It generally refers to sections or portions of the wire relative to each other, rather than referring specifically to a tip or terminating end of the wire. Accordingly, the proximal end 26 of wire 24 refers to that portion or section which moves into and/or through the needle while the distal end 28 of the wire refers to that portion or section of the wire which is releasably coupled with the slide 18 and moved by the slide to push the proximal end of the wire into position in the tissue workspace.

FIGS. 4A-4F illustrate use of the present invention and an inventive method for performing a Seldinger technique or other technique for positioning a wire and other elements, such as a catheter, into the vasculature of a patient or some other cavity or workspace. Device 10 is gripped by the hand 40 of a user for engaging the syringe. Specifically, the fingers of the hand are positioned at the various grip portions 16 and 22 of elements coupled with or part of the syringe. Generally, the grip portion 16 of the housing are held by the hand 40 and fingers of a user while the index finger or another finger is positioned proximate the grip portion 22 of the slide 18 for moving the slide with respect to the housing. In that way, the syringe body and plunger are engaged for movement.

Figure 4A:
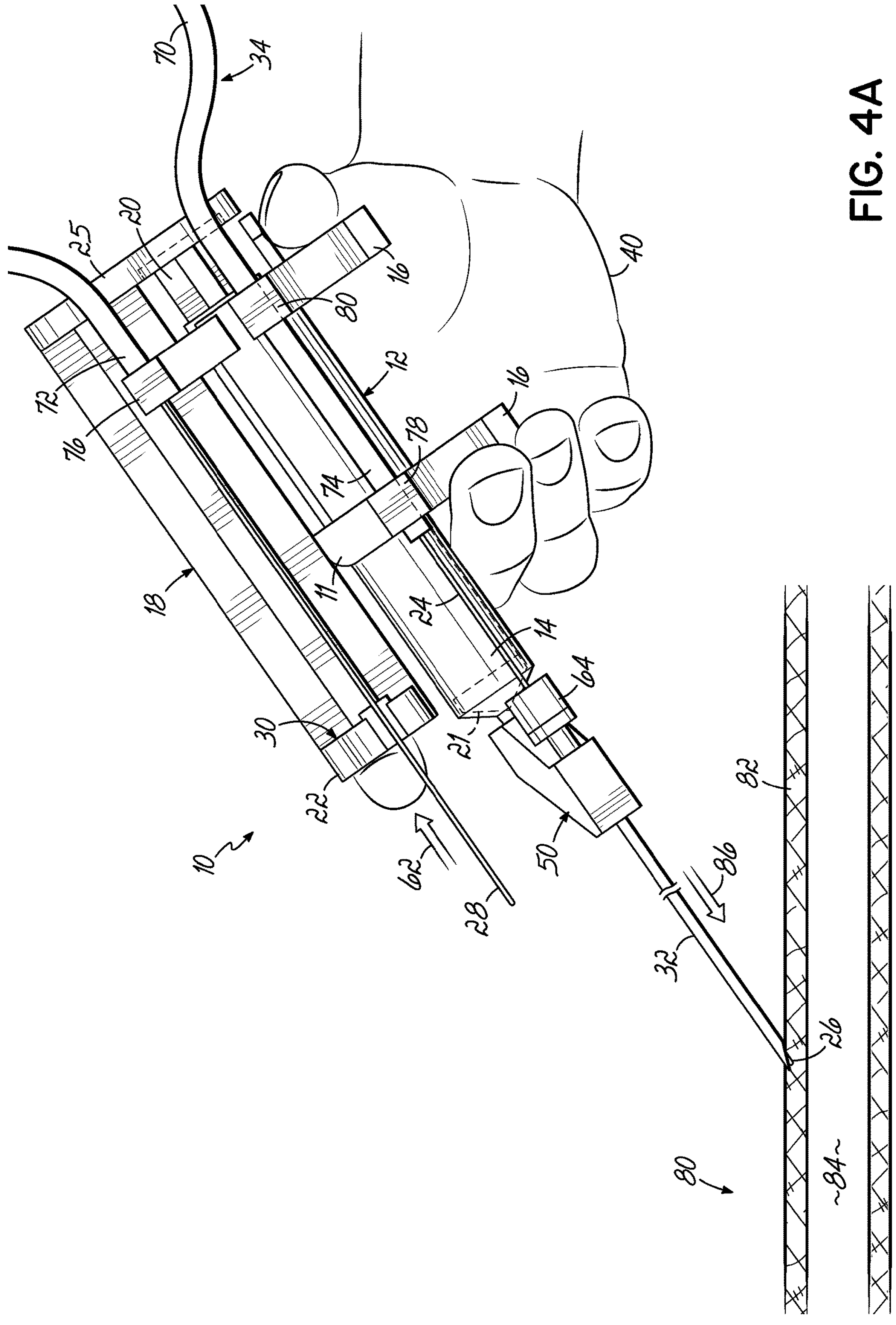
FIG. 4A is a side view of the wire and catheter placement device of FIG. 1, in a forward position, inserting a wire into tissue.

FIG. 4A shows vasculature of an animal, such as a human that includes one or more layers of skin or tissue 82, which confine or define an internal passage (workspace) 84 that carries the blood of the patient. Device 10 is gripped and the needle 32 is positioned against the skin 82 and is pushed in the direction of arrow 86 into the skin and subcutaneous tissue reflected by reference element 82. The tip 39 of the needle 32 and its bore are blocked initially by the skin and subcutaneous tissue 82. A retraction force in the direction of arrow 62 on grip portion 22 by the finger of a user's hand will move the plunger and create and draw a negative pressure within the syringe body 14 because the needle tip is blocked. Typically, the movement as shown of slide 18 will seek to move plunger 20 from the forward position to the retracted position and thus seek to draw air or fluid into needle 32. However, since the needle tip 39 is within the subcutaneous tissue or skin 82, no air or fluid can enter the needle 32. Therefore, a negative pressure or vacuum is created within the syringe body 14 and particularly within internal space 19 of the syringe body as the user seeks to move slide 18 and draw in fluid/air. Generally, the wire of 24 will be threaded into needle 32, and may be threaded a distance sufficient to be proximate to the tip 33 at the start of the process. As shown in FIG. 4A, the proximal end of the wire may be right at the tip 39 or rearwardly of the tip as it is passed into the tissue 82. The slide 18 may be slightly movable in the direction of arrow 62 before the plunger meets significant resistance from the vacuum drawn within the syringe body 14. Since movement of the plunger 18 and the associated wire gripping structure 30 will move the wire 24 slightly, generally it is desirable to position the tip of the wire proximal end 26 or the terminal end of the wire to be slightly back from the tip 39 of the needle at the beginning of the procedure so that it will not pass out of the needle at the short initial drawing of the plunger and vacuum. The distance may be determined by the size of the syringe body/plunger and can be adjusted by a user as desired by moving the wire manually within the gripping structure 30 so that the device 10 may be customized to a desired amount of negative pressure and slide movement before the distal end of wire moves out of the tip of the needle 39. In some embodiments, the wire might be 1-2 centimeters back from the tip. The space 84, such as a workspace within vasculature defined by tissue 82 is the ultimate target for the tip of the needle 39 as well as the wire 24.

Figure 4B:
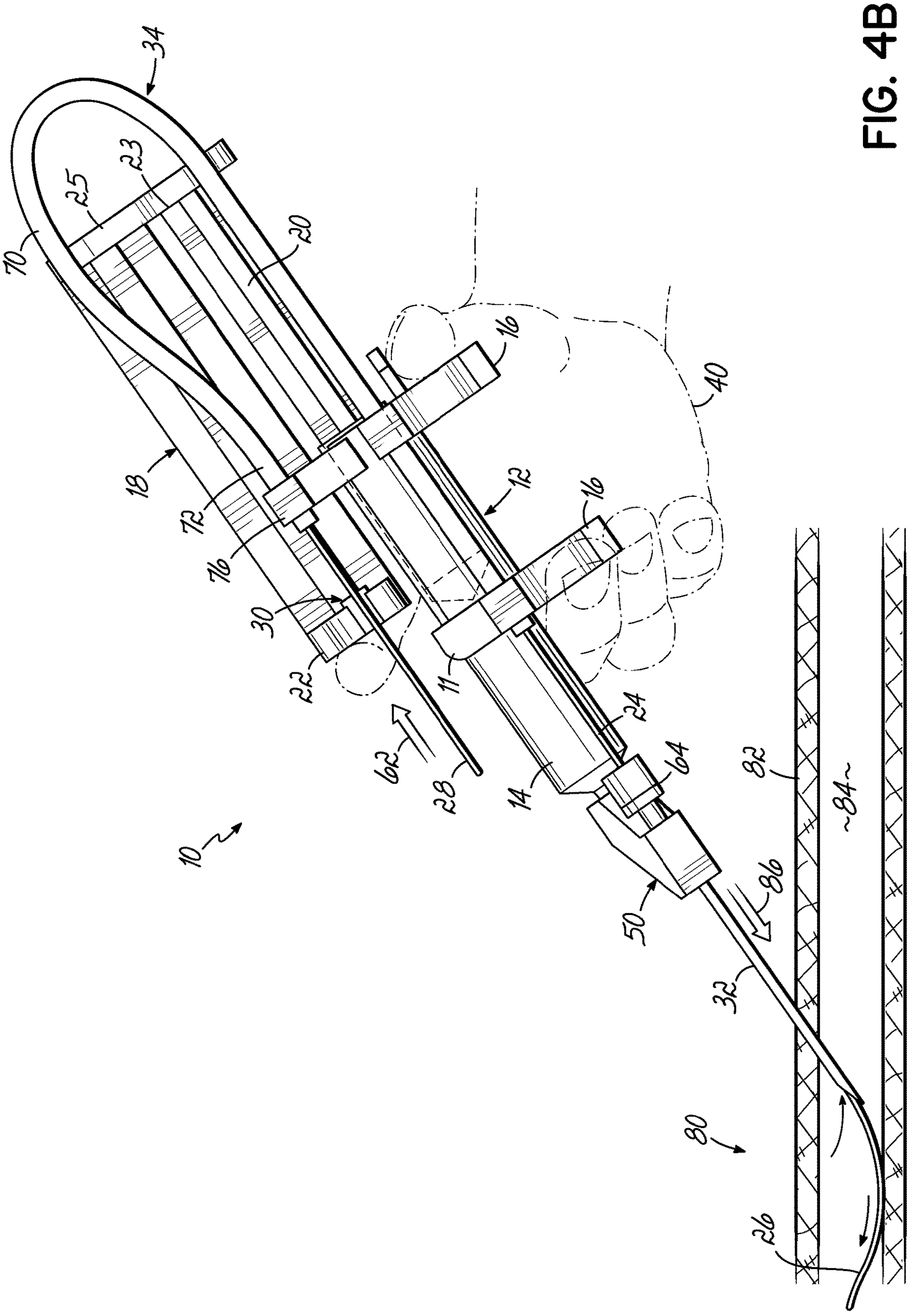
FIG. 4B is a side view of the wire and catheter placement device of FIG. 1, in a retracted position, inserting a wire into a workspace in tissue.

Referring to FIG. 4B, once needle 32 is passed through the tissue 82 and into space 84 fluid/air may be drawn in and there is no longer negative pressure or a vacuum. Therefore, the slide 18 and syringe plunger 20 may be moved more easily in the direction of arrow 62. That is, with the needle tip 39 in space 84 and without the vacuum, the slide and syringe plunger may be drawn further back to the retracted position as illustrated in FIG. 4B. With that movement, the distal end 28 of the wire 24 is moved toward the wire advancing mechanism 34. That is, with the loop guide 70 embodiment illustrated in FIGS. 4A-4F, the wire is moved toward and through the loop guide 70 and the direction is reversed to move the wire proximal end 26 in the direction of the needle, reflected by arrow 86 as shown in FIG. 4B. That is, in accordance with one aspect of the invention, the wire advancing mechanism is configured for translating or reversing wire movement and advancing the proximal end 26 of the wire forwardly into and through the needle when the slide 18 moves the syringe plunger 20 from the forward position to the retracted position. As will be appreciated, the retracted position may be any position in the syringe body rearwardly of the most forward position wherein a vacuum is drawn. Therefore, the retracted position is generally relative to the forward position rather than being an absolute rearward position of the syringe plunger in the syringe body.

A user controls the retraction of the slide and plunger. As the distal end 28 of the wire is moved rearwardly with the slide 18, the proximal end of the wire 24 is advanced through needle 32 and into the target space 84. As noted, while the example set forth herein discusses movement of the wire into vasculature, the target space may be any suitable vessel, abscess, or body cavity or other target of a patient and thus using the device 10 is not limited to a specific vasculature, although vasculature is used herein as a term to generally note the target space of the wire in the patient.

Once the wire 24 has been entered into the target space, the distal end 28 of the wire may be removed from the wire gripping structure 30. To that end, the gripping structure 30 might include lever arm 31 as shown in FIG. 1 which may be compressed in order to open up the wire gripping structure 30 to release the distal end 20 of wire 24. Thereafter, the wire 24 is free to be manipulated by a user rather than being coupled to slide 18 and the plunger. Since the wire 24 is already well within the target space 84, small, unintentional movements of the wire by a user will not remove it from the target space 84. Referring to FIG. 4B, the wire 24 is generally grippable at the exposed sections reflective of the distal end 28 as well as the portion of the wire proximate housing 12 that is rearward of the proximal end 26. A user can grip the wire at either of the exposed locations for further manipulation. For example, while the device 10 is held by one hand, the other hand of a user could be used to advance the wire further. Once the wire has been advanced to a desirable distance within space 84, it can be used for inserting other elements into the target space 84. For example, the wire can be used to advance a catheter with a dilator into the space.

Figure 4C:
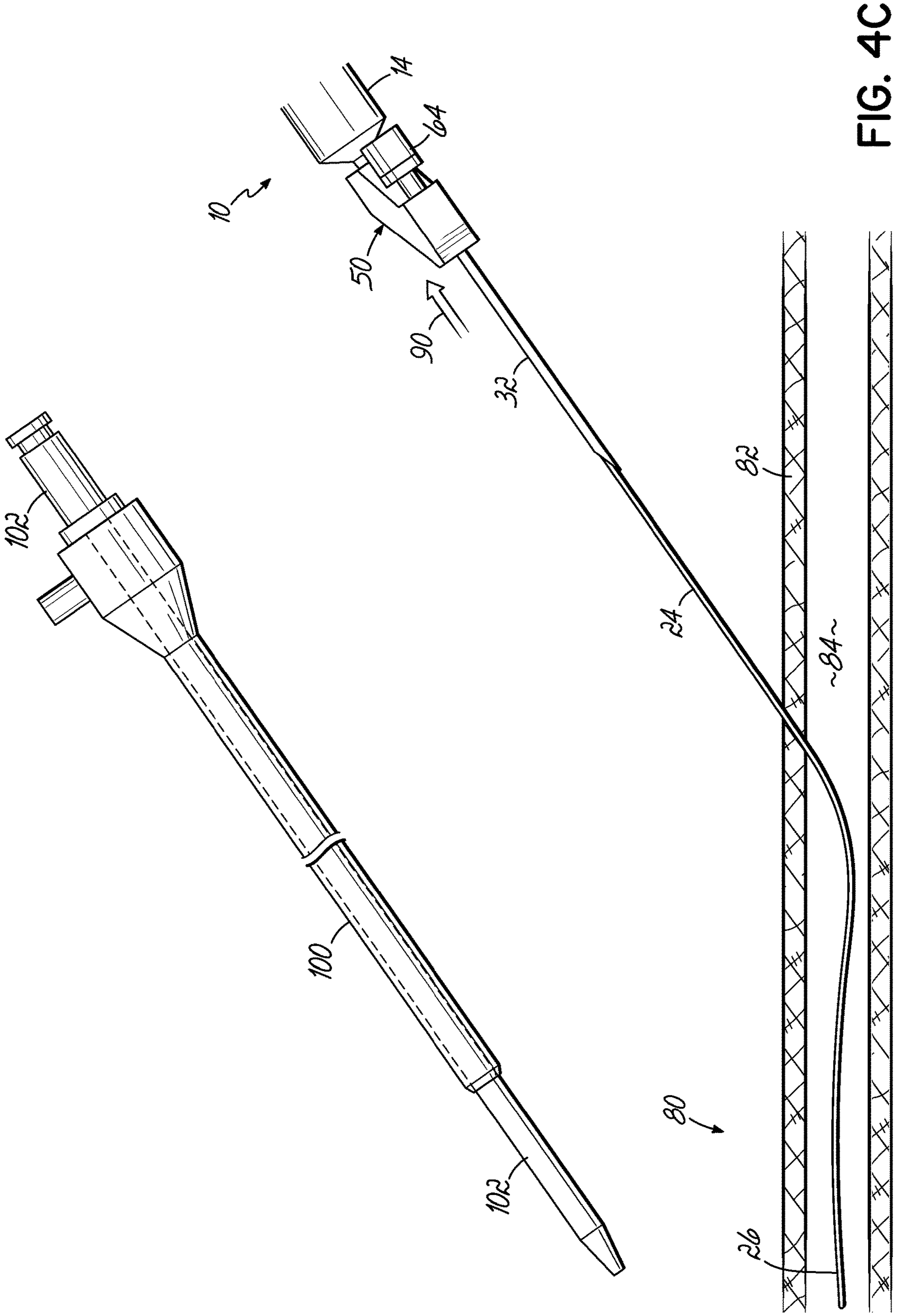
FIG. 4C is a side view of the wire and catheter placement device of FIG. 1, showing a catheter arrangement for insertion into a workspace in tissue via a wire.

Referring to FIG. 4C, device 10, and particularly the needle 32 and needle mount 50, may be removed from the wire. However, it may be desirable initially to only remove the syringe body and the rest of the device from the needle mount and leave the needle in place for additional procedures. For example, a Fabian test can be performed by hooking up tubing to the opening in the needle mount coupled with vacuum passage 54, or to the passage initially coupled with the syringe body 14. For procedures such as the positioning of a catheter 100, the device 10, including the needle 32 and needle mount 50 are removed and pulled up the wire as shown in FIG. 4C. Specifically device 10 and needle 32 and needle mount 50 can be removed in the direction of arrow 90 from the wire 24 positioned in space 84. The wire 24, in one use, may be for the purpose of guiding and positioning a catheter into the target space 84, such that wire 24 is used for guidance. Referring again to FIG. 4C, a catheter 100 around a dilator 102 to be threaded onto the distal end 28 of the wire once device 10 and needle 32 have been removed.

Figure 4D:
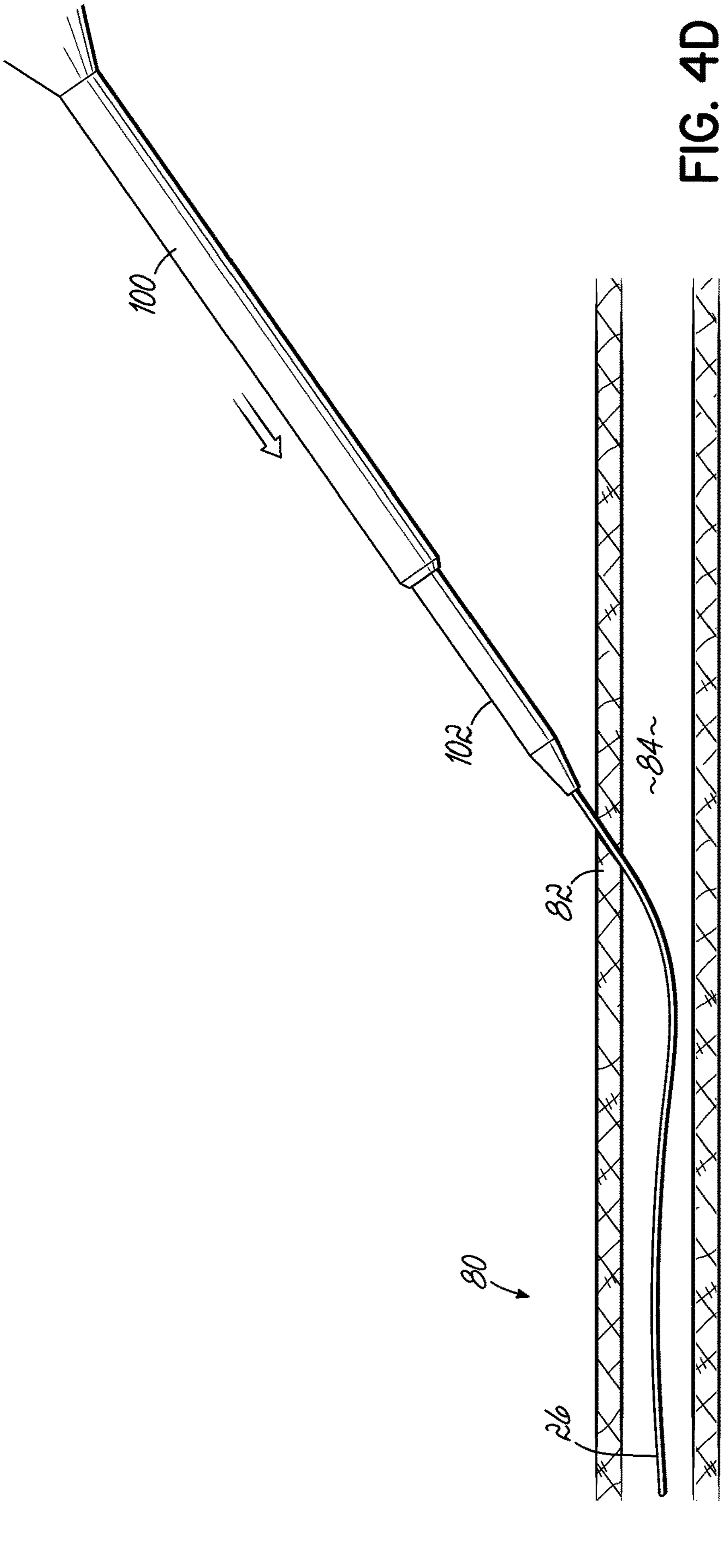
FIG. 4D is a side view showing a catheter arrangement for insertion into a workspace in tissue via a wire inserted in accordance with an embodiment of the invention.
Figure 4E:
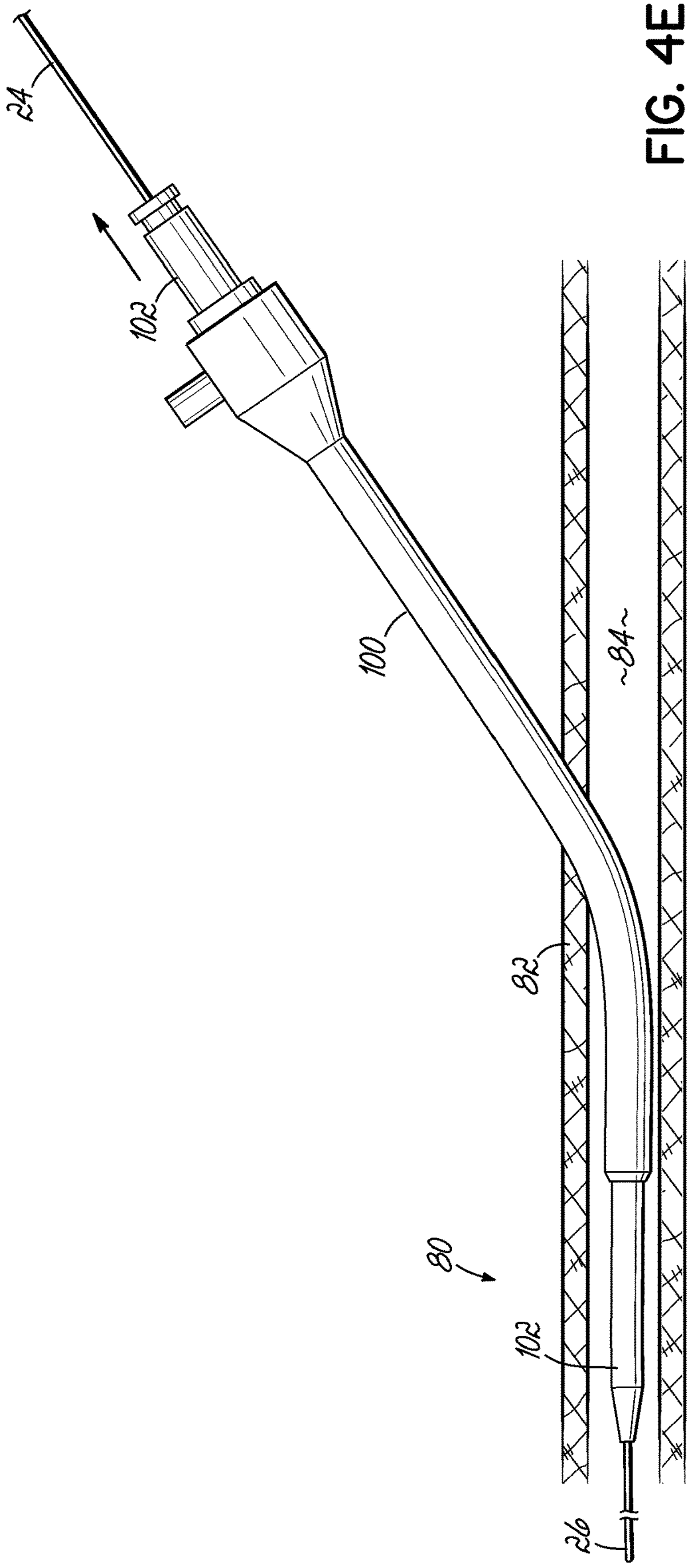
FIG. 4E is a side view showing a catheter arrangement inserted into a workspace in tissue via a wire inserted in accordance with an embodiment of the invention.
Figure 4F:
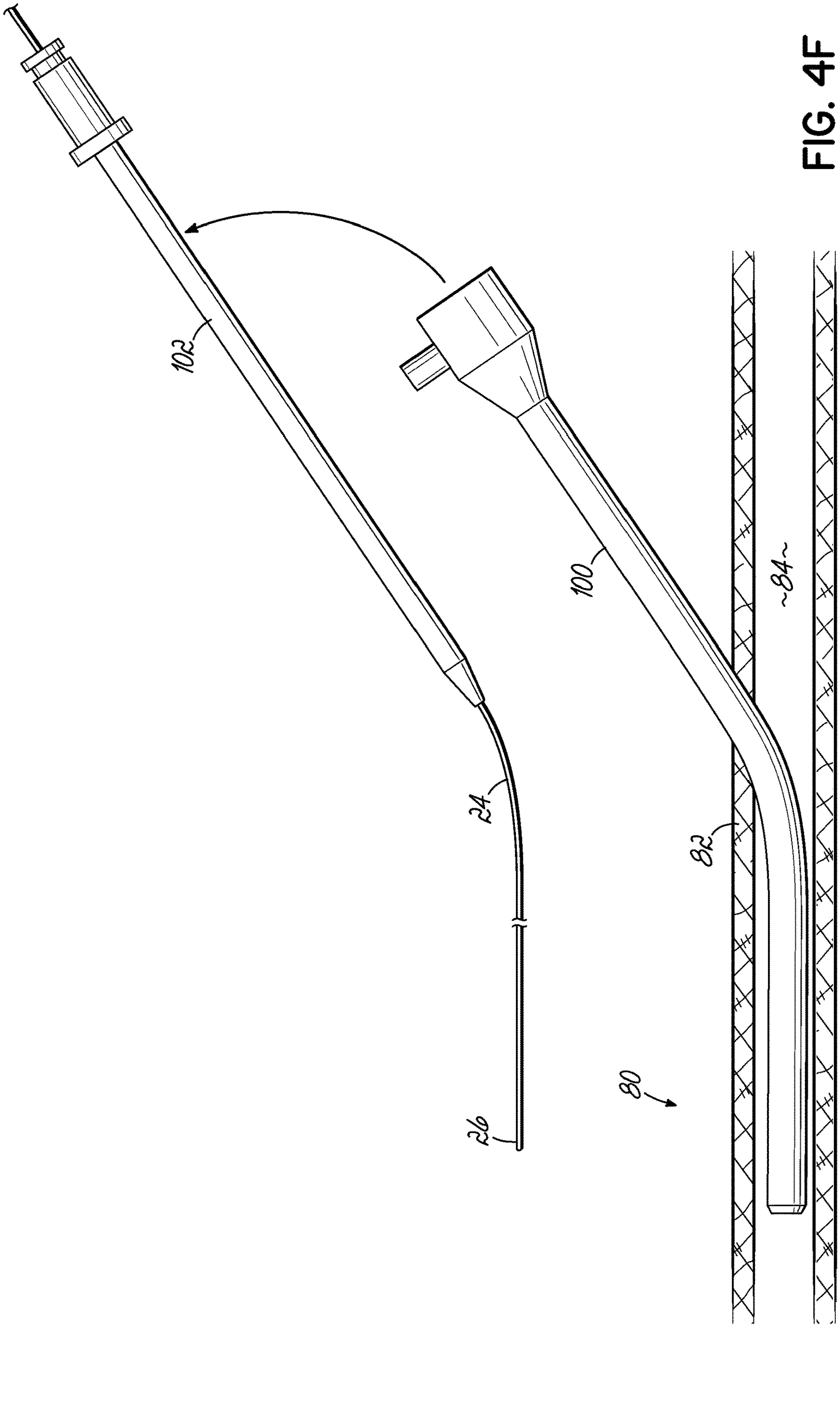
FIG. 4F is a side view showing a catheter inserted into a workspace in tissue via a wire inserted in accordance with an embodiment of the invention.

Referring to FIG. 4D, once the wire 24 has been threaded into the dilator 102 and catheter 100, those elements may be slid through the opening in tissue 82 and the same opening utilized to insert the wire. As shown in FIG. 4E, dilator 102 and catheter 100 can then be positioned in space 84 for further procedures. Then, wire 24 and/or dilator 102 may be removed from the catheter 100 and space 84 as illustrated in FIG. 4F. Wire 24 may be removed first and then the dilator 102 or they could be removed simultaneously to leave the catheter 100 in position for the performance of further procedures within the target space 84, such as vasculature.

The device 10 provides significant advantages over techniques for introducing and advancing a wire and other elements within a target space of a patient. Device 10 directly couples the drawback of a syringe plunger to the advancement of wire 24 via the releasable wire gripping structure of 30. The same force that is used to move the slide and plunger is generally the same force used to move the wire into the needle and the workspace. That is, there are no intervening mechanisms in device 10 so that the wire movement haptic feedback is directly to the plunger and slide and a user's fingers. The wire may then be advanced once the needle tip enters any target vessel, abscess, body cavity, or other space. With a single hand, a user can position the wire within the target space. The function of the syringe body 14 and the movement of the syringe plunger therein through slide 18 and the wire movement through loop 70 is the only resistance encountered by a user and thus allows for greater haptic feedback in the process. The direct coupling between movement of the syringe plunger and simultaneous advancement of the wire allows a user to have a better feel of how the wire is advancing and provides faster feedback that the wire may not be advancing appropriately. For example, if the wire runs into the wall of a vessel or an occlusion or if the needle is withdrawn from the target space prior to wire advancement, a user has immediate feedback via the housing and slide and the grip portions 16 and 22 provided on the housing 12 and slide 18. Furthermore, the wire 24 advances external to the syringe housing 12 or syringe plunger as illustrated in FIG. 1. As discussed further herein, this allows for other elements to be preloaded onto the wire for placement using the wire in target space 84.

The present device 10 and other alternative embodiments of the invention as described herein, can be held in one hand for use to provide a generally single movement. In an alternative embodiment, engagement by a robot rather than a hand might be used. The wire can be advanced with the same hand or movement that pulls the syringe plunger. A user is controlling the advancement of the wire and no spring, lever intervening, or other mechanism removes that control from a user. If the wire meets resistance as felt in the device, a user can stop moving the plunger and advancing the wire. Furthermore, an additional advantage is that the device 10 and its related embodiments allow for a longer wire to be used. The wire advancing mechanism 34, particularly the loop guide 70 or other guide structure, can be configured and dimensioned based upon the desired length of the wire. The additional wire can then allow catheters/sheaths and dilators to be preloaded onto the wire for introduction into the target space over the wire as discussed further herein. In accordance with another feature of the invention, different sizes of syringe bodies 14 may be used with different amounts of fluid from the target space correlated to a greater or lesser movement of the wire based upon movement of the slide and wire gripping structure 30. That is, if a syringe body 14 and syringe plunger having a larger diameter are used, more air/fluid is needed to translate the slide rearwardly and move the syringe plunger to the retracted position at a certain distance. If it is preferable to have a more minimal amount of air/fluid through the syringe to advance the wire a desired distance, a smaller diameter syringe body 14 and syringe plunger 20 may be used. The wire and syringe decoupling, so that the wire can be advanced independently of fluid draw, and the ability to adapt the fluid draw is useful if a target space is small. If significant fluid draw may collapse a target space, this ability to move the wire without too much draw or independently of further draw is advantageous.

In the present invention, with the single hand of a user, the entry of the target space can be determined and the slide 18 and syringe plunger 20 moved rearwardly to a retracted position while the wire is advanced forward simultaneously and generally in a single stroke. Furthermore, the force that is used to advance the wire is created directly by a user and thus can be more sensitively and accurately applied as opposed to another mechanism, such as a spring or lever that advances the wire. That is, there is generally a 1:1 ratio of force to draw the plunger and advance the wire using device 10. This provides for very sensitive feedback in use of the device and movement of the wire to the user through the user's hand.

The present device 10 and other disclosed embodiments can be used with a range of needle sizes, syringe body sizes, and wire sizes. A tapered wire may be used for the wire element to allow fluid in the needle to easily progress past the wire into the syringe body. Furthermore, a wire with a coiled wire tip might be utilized while the rest of the wire is smooth. In that way, the seal around the wire could be airtight, but the fluid/air could more easily go around the tip of the wire into the needle. As noted, the housing 12 and syringe body 14 may be formed such that they are a unitary piece. Similarly, the slide 18 and syringe plunger 20 may be formed together as a unitary piece. Then the syringe plunger with grip portions and a wire gripping structure would engage the syringe body with its own grip portions to provide the desired interaction of the components. Alternatively, the housing 12 and slide 18 may be configured separately from the syringe components. In such a case, syringe body 14 would fit or snap or otherwise couple with the appropriately constructed housing 12 while the syringe plunger 20 would fit into or snap or otherwise couple appropriately with the slide where the slide 18 and syringe plunger interact as disclosed.

The wire gripping structure 30 as illustrated in FIGS. 1 and 2A may be a clamp type structure with opposing clamp ends 35 biased together to frictionally grip or clamp wire 24 at its distal end 28. The lever structure 31 as shown in FIG. 1 may be operated to open and close the clamp ends 35 for gripping or releasing the wire 24. The pair of clamp ends may be utilized to releasably grip the distal end of the wire. The grips should be tight enough to provide the necessary movement of the wire upon moving the slide 18 and the plunger to a retracted position under the force of a user's hand. Other wire gripping or wire clasping structures may also be used as long as the wire is releasable from the plunger/slide movement.

The present invention provides an ergonomic advantage and stability utilizing a single hand of a user. The grip portions 16 that extend from housing 12 allow for the thumb and one or more of the middle fingers to hold the device and stabilize the syringe body for example. The grip portion 22 positioned at the forward end of the slide 18 allows the index finger on the same hand to easily and comfortably move the plunger and draw negative pressure and then subsequently advance the wire upon the needle entering the target space. The thumb and one or more middle fingers can firmly support the device 10 and syringe body while the index finger can separately control the motion of the slide, syringe plunger, and the wire. This allows a user to keep the needle tip very steady to prevent removal of the needle from the target space while the wire is simultaneously being advanced.

Figure 5:
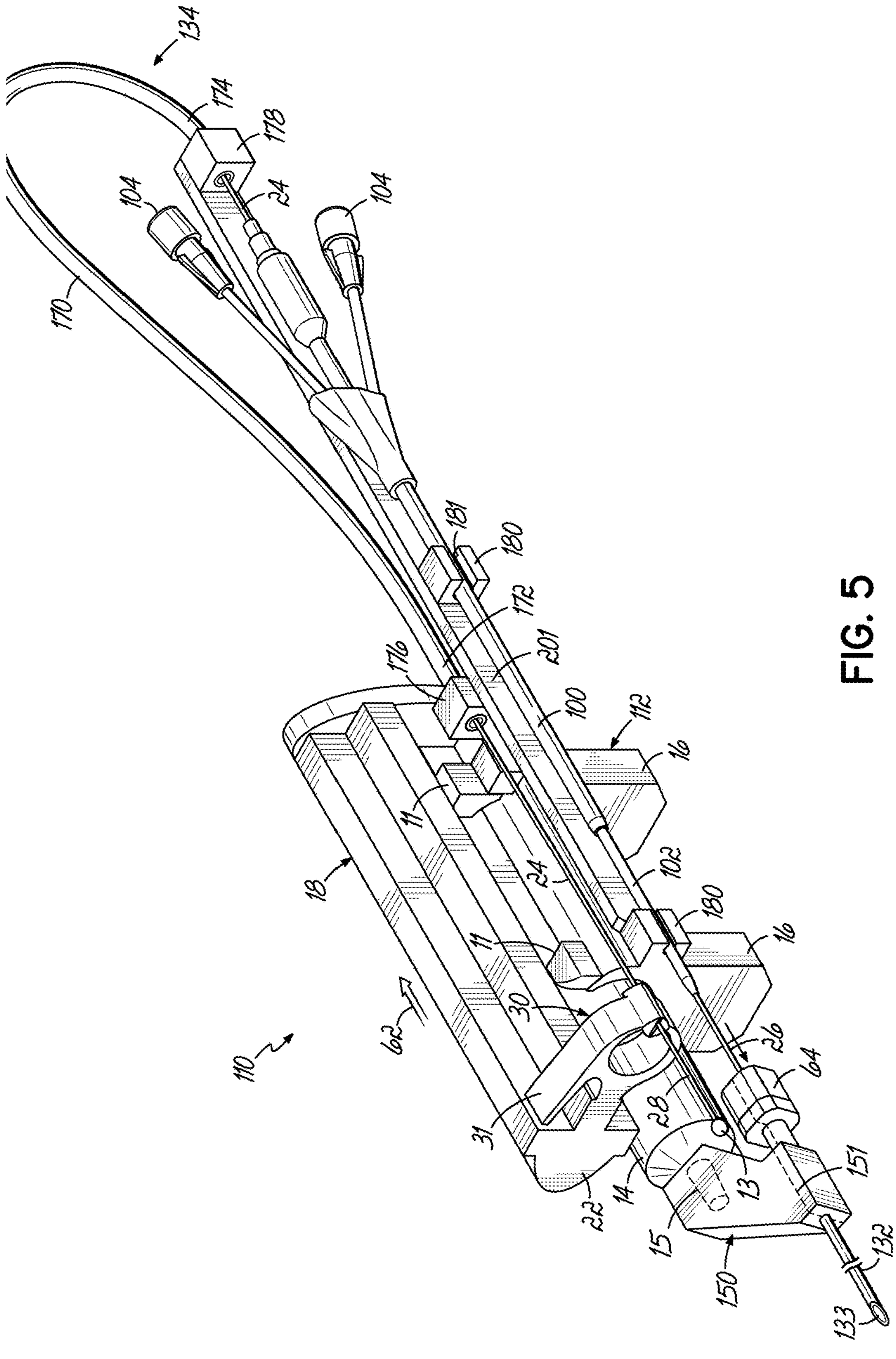
FIG. 5 is a perspective view of wire and catheter placement device in accordance with another embodiment of the invention.

FIG. 5 illustrates an alternative embodiment of the device 110 similar to device 10 but providing for the advancement and positioning of a wire preloaded with a catheter, dilator or other element into a target space in tissue, such as into the vasculature of a human. As with other embodiments of the invention, such wire advancement can be used for a number of different medical procedures. Similar elements between the devices 10 and 110 will share some common reference numerals for common elements. The device 110 includes a housing 112 that includes or is configured for coupling with a syringe body 14 and grip portions 16 for engagement by a user. As with device 10, the housing and grip portions could be part of a unitary syringe body or separate from the body. A slide 18 is positioned adjacent housing 14 and is part of the plunger or configured for coupling with a syringe plunger 20. The syringe plunger 20 moves inside the syringe body 14 between a forward position as illustrated in FIG. 6B, for example, and a retracted position as illustrated in FIG. 6C. The slide 18 also includes a grip portion 22 for engagement by a user to move the slide 18 and the syringe plunger 20 with respect to the housing 112. Specifically, the slide 18 moves the syringe plunger 20 from the forward position to the retracted position during the use of the device 10. As described herein, the housing 112 may be dimensioned to accept a catheter arrangement in front of the wire advancing mechanism.

Device 110 also includes a wire 24. The wire 24 includes a proximal end 26 and a distal end 28. The slide 18 also includes a wire gripping structure 30 that releasably grips the distal end 28 of the wire for facilitating movement of the wire as described herein. In the embodiment of the device 110 illustrated in FIG. 5, the wire 24 is preloaded with other components to be inserted into the target space in the tissue as guided by the wire. Specifically, as illustrated in FIG. 5, a dilator 102 and catheter 100 (i.e., catheter arrangement) are loaded onto the wire. The catheter 100 may include one or more ports 104 that feed into the catheter depending on the medical procedure for which the catheter will be used. A needle 132 is coupled with the syringe body 14 and is also configured for guiding the proximal end 26 of the wire into a workspace, such as a vasculature space, in accordance with features of the invention. Similar to device 10, the movement of the slide 18 and syringe plunger 20 rearwardly away from the needle 132 and the body will draw a negative pressure and will also seek to advance the wire 24 through a bore of needle 132 into the vasculature or other target space in a single movement.

To that end, a wire advancing mechanism 134 is coupled generally between the slide 18 and housing 112 as seen in FIG. 1. The wire advancing mechanism 134 guides the wire and is configured for advancing the proximal end 26 of the wire forwardly into needle 132 when the slide 18 moves the syringe plunger 20 from the forward position to a retracted position as illustrated in FIG. 6C.

The purpose of the wire advancing mechanism is to reverse or translate the rearward movement of the slide 18 and the accompanying movement of the syringe plunger 20 to the retracted position and create a forward movement of the wire 24 into and through the needle 134 in one movement stroke. As described herein, a hand of a human operator or some other mechanism, such as a robot, engages the respective grip portions 16 and 22 of the respective housing and slide and moves the slide 18 rearwardly toward a retracted position along the housing as illustrated in FIGS. 6B and 6C. The wire gripping structure 30 of the slide 18 grips the distal end 28 of the wire. The movement of the slide 18 and syringe plunger 20 to a retracted position causes the distal end 28 of the wires to move through the wire advancing mechanism 134. The wire advancing mechanism reverses or translates that rearward movement of the wire distal end into a forward movement of the wire proximal end 26 into and through the needle 132. As the slide 18 and plunger 20 are moved to the retracted position, the proximal end 26 of the wire is simultaneously advanced through the needle, and ultimately into the target space into which the needle is inserted as described herein.

Figure 6A:
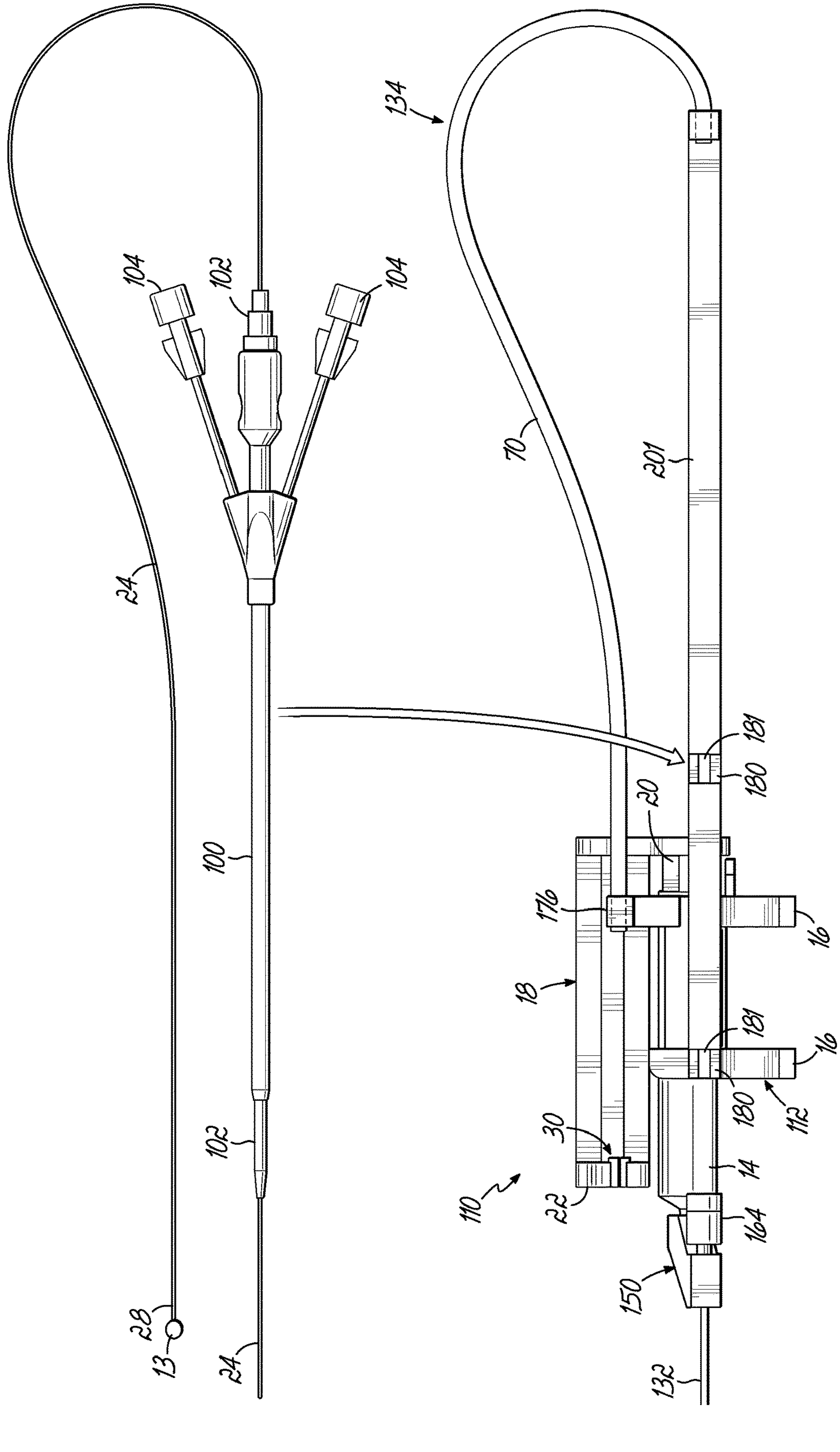
FIG. 6A is a side view of the wire and catheter placement device of FIG. 5, in a forward position, with a wire and catheter arrangement for placement in the device.
Figure 6B:
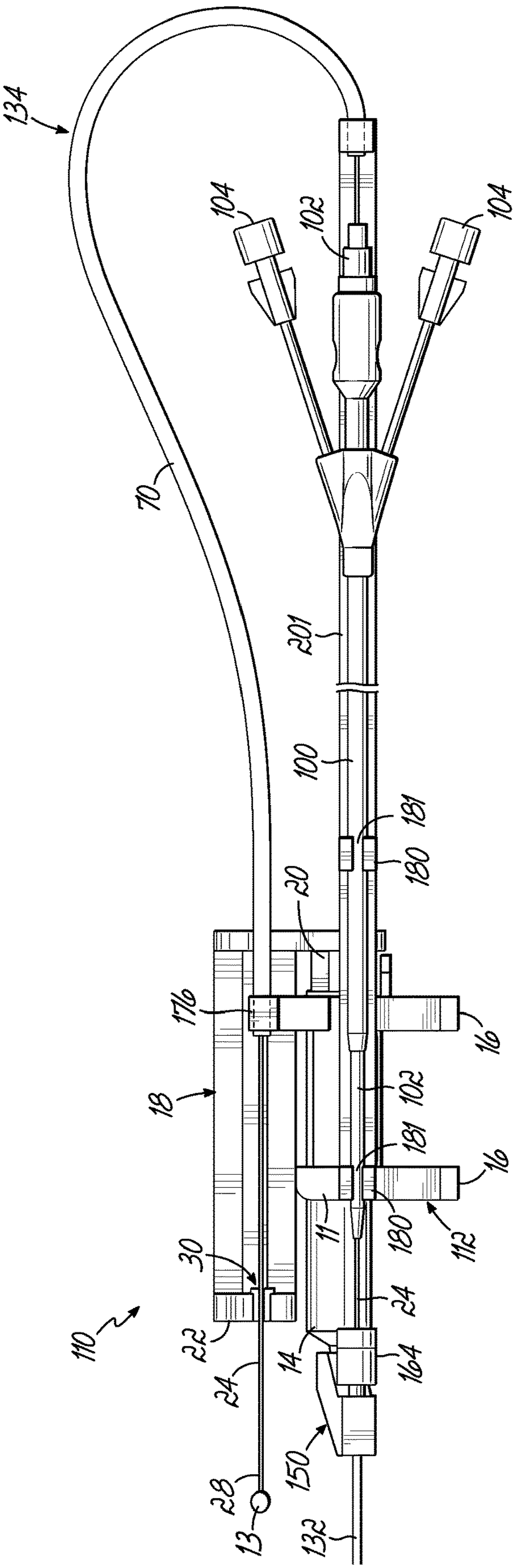
FIG. 6B is a side view of the wire and catheter placement device of FIG. 5, in a forward position, with a wire and catheter arrangement in the device.
Figure 6C:
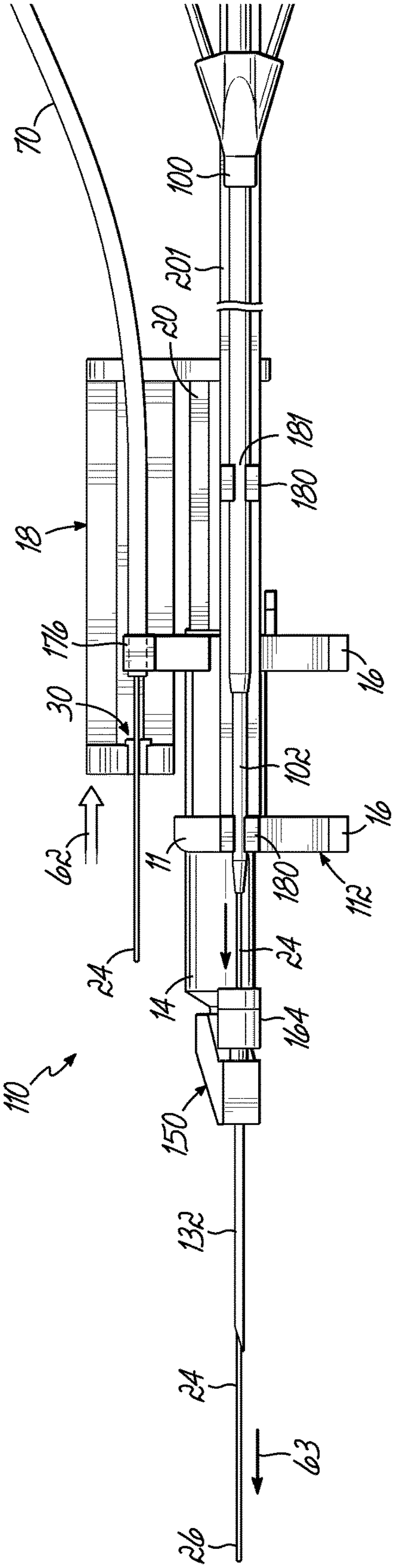
FIG. 6C is a side view of the wire and catheter placement device of FIG. 5, moving to a retracted position, to advance a wire for placement of the catheter arrangement.
Figure 6D:
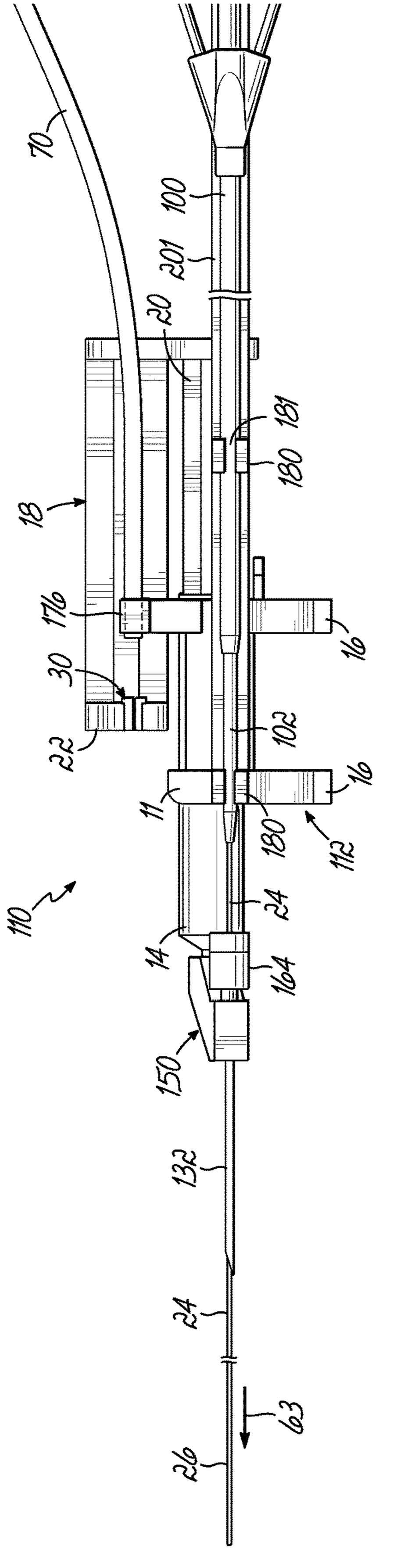
FIG. 6D is a side view of the wire and catheter placement device of FIG. 5, in a retracted position, with an advanced wire for placement of the catheter arrangement.
Figure 6E:
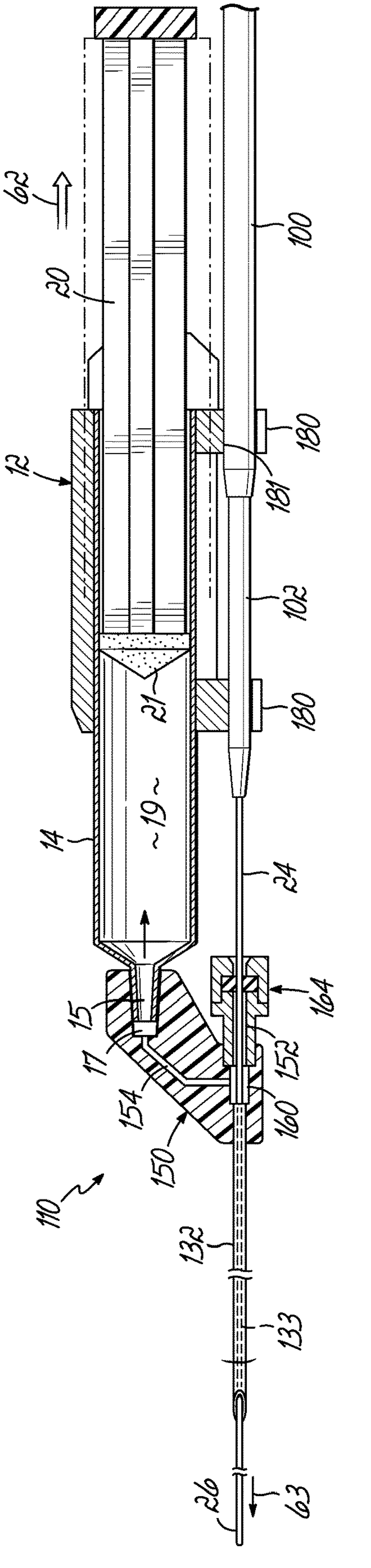
FIG. 6E is a top view, in partial cross-section, of the wire and catheter placement device of FIG. 5, in a retracted position, with an advanced wire for placement of the catheter arrangement.
Figure 6F:
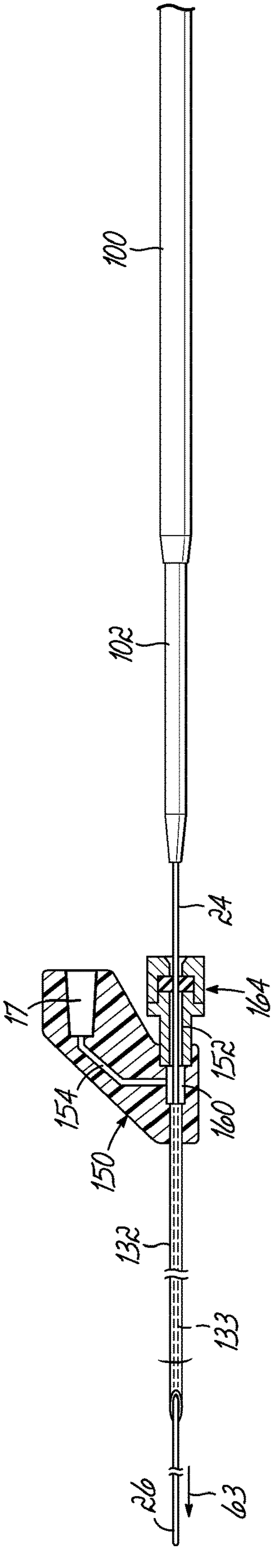
FIG. 6F is a top view, in partial cross-section, of the wire and catheter arrangement of FIG. 6E, with most of the wire and catheter placement device of FIG. 5 removed.
Figure 6G:
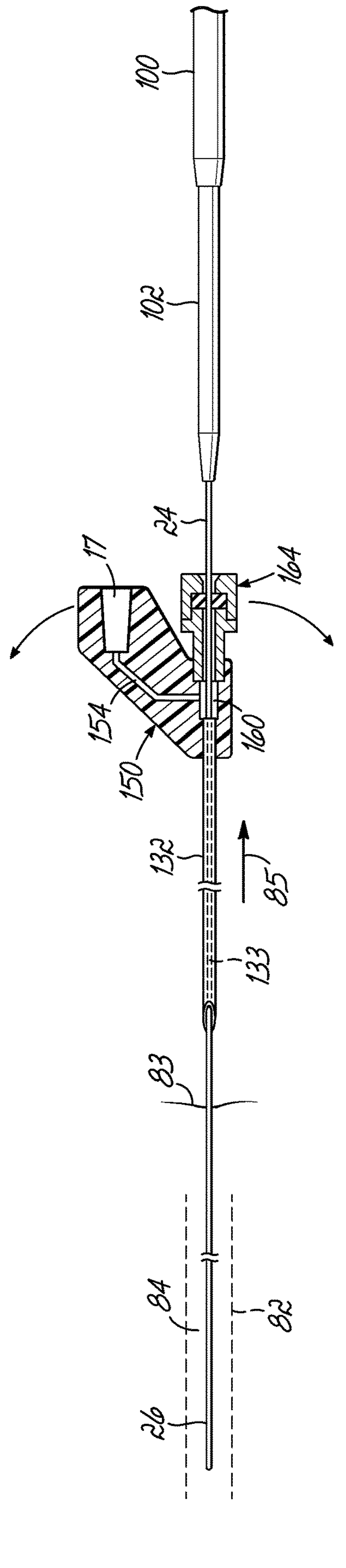
FIG. 6G is a top view, in partial cross-section, of the wire and catheter arrangement of FIG. 6F to be inserted into a workspace in tissue via a wire inserted in accordance with an embodiment of the invention.
Figure 6H:
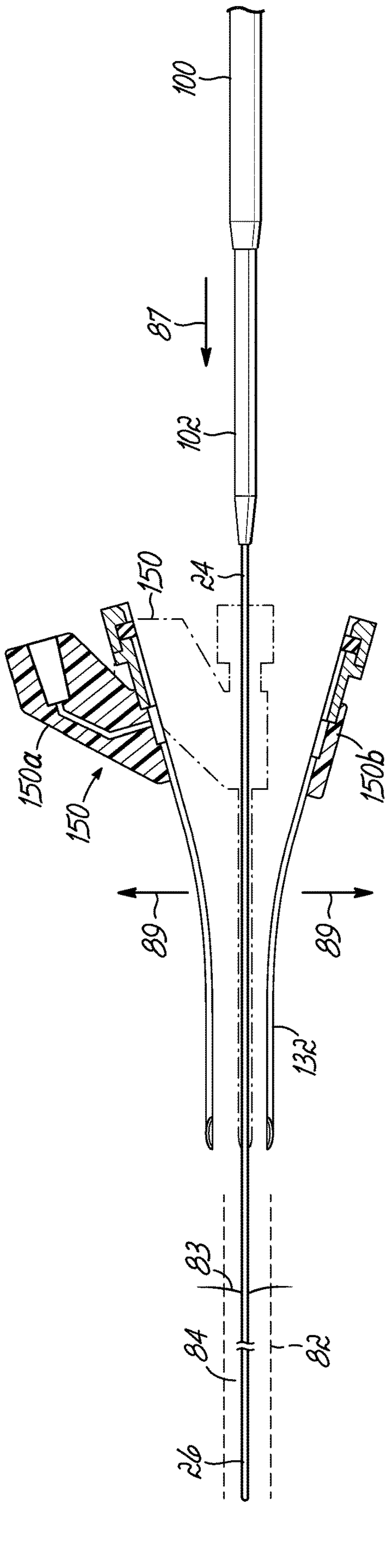
FIG. 6H is a top view, in partial cross-section, of the wire and catheter arrangement of FIG. 6G to be inserted into a workspace in tissue, with a removal of the needle.
Figure 6I:
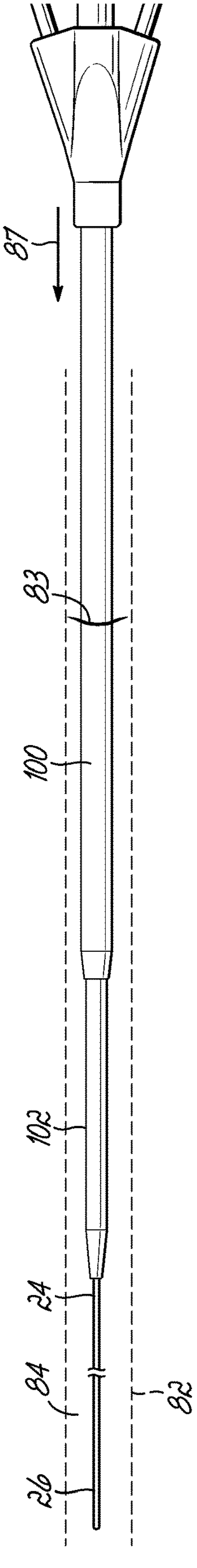
FIG. 6I is a top view, in partial cross-section, of the wire and catheter arrangement of FIG. 6G inserted into a workspace in tissue.
Figure 6J:
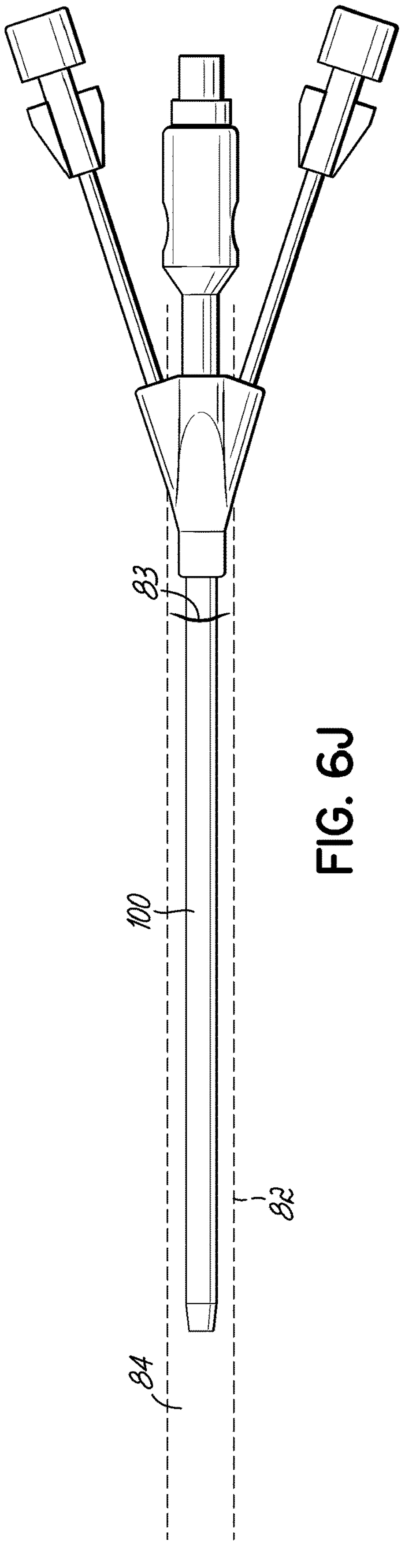
FIG. 6J is a top view, in partial cross-section, of the catheter arrangement of FIG. 6I inserted into a workspace in tissue, with a dilator removed

In the embodiment illustrated in FIGS. 5-6J, the housing 112 is configured to space the wire advancing mechanism 134 further rearwardly of the housing 112. In accordance with the invention, the wire advancing mechanism 134 operates similarly to mechanism 34 and guides the wire and is configured for advancing the proximal end of the wire forwardly into and through the needle when the slide moves the syringe plunger from the forward position to the retracted position. The wire advancing mechanism 134 is positioned to allow for the pre-threading or pre-positioning of other elements, like a dilator 102 and catheter 100 onto the wire before it is inserted into the workspace. The housing is configured to secure the catheter arrangement. This then presents the catheter for placement immediately upon placement of the wire. The wire advancing mechanism 134 also includes a loop guide 170 and is generally positioned between the slide 18 and housing 112 so as to provide forward translation of the wire proximal end with respect to the rearward or retracting movement of the slide 18 and syringe plunger. Specifically, referring to FIG. 5, the wire advancing mechanism 134 includes a loop guide 170 that has an input end or distal end 172 positioned to receive a wire from the wire gripping structure 30 of the slide 18 and an output or proximal end 174 for guiding a proximal end of the wire 24 and outputting the wire into a catheter 100 and through the catheter and ultimately into and through a needle mount 150 and then ultimately into and through the needle 132. The loop guide 170 may be a closed tube as illustrated in FIG. 5. Alternatively, the loop guide might be open with an appropriate configuration and structure for capturing wire 24 and guiding it through the loop guide from the distal end 172 to the proximal end 174. As illustrated in FIG. 5, the housing 12 may be appropriately formed to include mount portions 176, 178 that interface with and contain the respective distal end 172 and proximal end 174 of the loop guide 170. In the embodiment 110 of the device, because of the clearance needed for handling the catheter arrangement, the housing 112 includes an extension section 201 that extends rewarding on the housing to position the mount portion 178 rearwardly from the mount portion 176. In that way, space is created forward of the mount portion 178 to position the catheter arrangement 100, 102 forward of the wire advancing mechanism 134 so that the wire can pass through the catheter arrangement on its path to the needle 132. That is, the wire advancing mechanism sits rearwardly of the catheter arrangement. More specifically, the output or proximal end 174 of the mechanism 134 sits behind the catheter arrangement so a wire can exit the output end and enter the catheter arrangement directly. For securing the catheter arrangement, one or more additional mount sections 180 may be implemented in the housing 12 and or on the extension section 201 for holding a portion of the catheter arrangement. Referring to FIG. 5, the additional mount sections 180 may have slots 181 formed therein for receiving the elements that make up the catheter arrangement. The catheter arrangement may be snapped into the slots 181 or otherwise secured. In a similar fashion as device 10, negative pressure or a vacuum may be drawn through syringe body 14 by movement of the slide/plunger in the direction of arrow 62 and simultaneously, the proximal end 26 of the wire will advance in the direction of arrow 63 or in the direction of the movement of needle 32 into vasculature or another workspace as described herein.

In the embodiment of the device 110, the needle structure has to accommodate the fact that it cannot be slid off of and removed from the wire in the same fashion as with device 10. This is because the catheter arrangement 100, 102 sits behind the needle and prevents the needle from being slid rearwardly and removed from the wire. Rather, the device 110 implements a needle 132 and needle mount 150 that may be broken away or disassembled in order to be removed from the wire. More specifically, the needle mount 150 may incorporate a weakened section, such as along score line 151, that will allow separation of the needle mount into halves or smaller sections to remove it from the wire 24 to then allow the catheter arrangement to be slid down in the wire into position in the workspace. The needle 132 is also in the form of a peel apart or break apart needle for facilitation of the removal of the entire needle mount 150 and needle 132.

More specifically, device 110 includes a suitable needle mount 150 for coupling the needle 132 with the device. Particularly, the needle mount 150 couples the needle 132 simultaneously with both the syringe body 14 as well as the wire 24. Referring to FIG. 6E, the needle mount 150 includes a guide passage 152 for directing movement of the wire 24 into and through the needle 132. The needle mount 150 also includes a vacuum passage 154 that is coupled with the syringe body 14 to create a negative pressure in the needle when the syringe plunger is moved to the retracted position as illustrated in FIG. 6E. As described herein, movement of the slide and the syringe plunger to the retracted position draws negative pressure within the needle 132 through needle mount 150 to prevent the rearward movement of the slide and syringe plunger to the retracted position. Once the needle penetrates into the vasculature or other workspace through the tissue, the needle tip is no longer blocked or occluded and the negative pressure is broken so that air/fluid from a workspace is drawn into the needle and syringe body. The slide and syringe plunger may then be easily drawn rearwardly in the device 110 to the retracted position as fluid/air is pulled through the needle. The movement of the slide/plunger also simultaneously moves the wire gripping structure 30 rearwardly with respect to needle 132 and thus pushes wire 24 through the wire advancing mechanism 134. This turns or reverses or translates the wire movement and advances the proximal end 26 of the wire forwardly through needle 132 as illustrated in FIG. 6D.

In the embodiment of the invention illustrated in 5, the needle mount 150 creates an airtight passage in both the vacuum passage 154 as well as the guide passage 152. The needle 132 is dimensioned so the needle bore allows for passage of wire 24 therethrough in addition to the simultaneous passage of air and/or fluid rearwardly through the needle 132 when the wire 24 moves forwardly within the needle. The needle mount 150 forms an intersection point 160 for the vacuum passage 54, the internal passage 133 of the needle, and the guide passage 52 for the wire 24. The mount 150 therefore operates similarly to the needle mount 50 illustrated in FIG. 1. To that end, the needle mount 150 also includes a sealing mechanism 164 that engages with guide passage 152 and wire 24 for providing the airtight seal in the guide passage. That is, the sealing mechanism engages with wire 24 as it passes through the sealing mechanism and into the guide passage 152 so that wire 24 may move through the guide passage of the needle mount and through needle 32 at the same time that negative pressure and/or fluid and air is being drawn through movement of the plunger 20 within the syringe body 14 as shown in FIG. 6E.

In accordance with one aspect of the invention, the housing 112 and syringe body 14 may be formed as a unitary structure wherein the housing is part of the syringe body. In another embodiment of the invention, the housing is configured to couple with a separate syringe body with the syringe body in a proper position with respect to the housing grip portions 16. Similarly, the slide 18 may be formed together with a syringe plunger as a single piece such that the slide and wire gripping structure are moved as the syringe plunger is moved. Alternatively, the slide 18 may be formed to couple to a separate syringe plunger in order to couple the movement of one to the other and the movement of the wire with the plunger. In that way, the device with a housing 12 and slide 18 might utilize a typical syringe having a syringe body and syringe plunger as shown in FIG. 1A.

FIGS. 6A-6J illustrates implementation use of the device 110 as illustrated in FIG. 5. Device 110 provides an all-in-one solution for delivery of the guide wire, catheter, and other elements to a target space. Referring to FIG. 6A, in use, the device 110 is loaded with a catheter 100, a dilator 102, and other elements, such as ports 104 that are preloaded or positioned on wire 24. As noted, the example and elements shown in FIG. 6A is not limiting and other elements might be preloaded onto wire 24. The housing 112 includes the mount sections 180 into which the catheter assembly may be loaded. For example, the mount sections 180 might clip on to catheter 100. The wire 24 can then be threaded through advancing mechanism 134 and through the catheter arrangement and into needle 132. The wire gripping structure 30 can be manipulated to grip the distal end, while the proximal end of the wire is threaded into the needle 132. FIG. 6B shows the device 110 loaded with a catheter arrangement and wire such that the catheter arrangement and the wire is in line with the housing 112 for performance of the procedure utilizing device 110. As illustrated in FIG. 6C, as the device 110 is used the grip portions 16 and 22 are engaged and pressure is applied to the slide 18 and grip portions 22 by movement of a user's finger in the direction of arrow 62. The wire 26 may be advanced into the target space. As discussed herein with respect to FIG. 4B, the wire will advance into the target space once the negative pressure is released and the plunger and the slide 18 are able to slide more freely rearwardly with respect to the syringe body and the housing 112. As shown in FIG. 6D, the wire will advance in the direction of arrow 63 as the slide 18 is moved further in the opposite direction toward a retracted position. This then positions the guide wire, in line with the catheter arrangement, for further insertion of the catheter arrangement into the target space. Referring to FIGS. 6E and 6F, the device 110 may be removed from the catheter arrangement and wire 26 once the wire is positioned into the workspace.

FIGS. 6E and 6F illustrate that once the wire has been positioned appropriately within the target space after penetration into the target space by the needle and the drawing of any air or fluid into the syringe body 14 as illustrated by arrow 15, then the device 110 is no longer needed. The catheter arrangement may be removed from the device 110. The device may be removed from the needle 132 and needle mount 150. FIG. 6F illustrates an exposed catheter 100, a dilator 102, and wire 24 with device 110 removed. The needle mount 150 remains in position with needle 132. Because of the in-line position of the catheter and dilator on and behind the wire 24 portion of the workspace, the needle mount 150 and needle 132 cannot simply be slid off the end of wire 24. To that end, in the use of device 110 with both the wire and in-line catheter arrangement, needle mount 150, and needle 132 must break away or tear away from wire 24.

Figure 12:
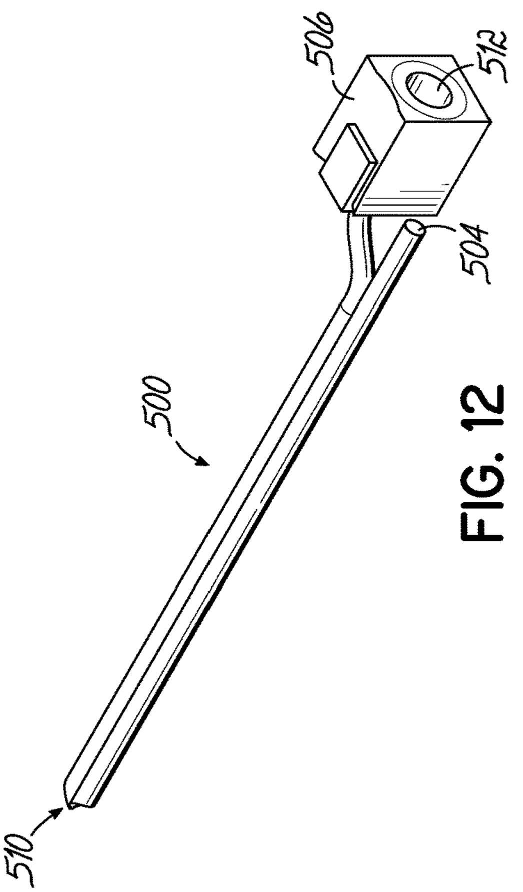
FIG. 12 is another perspective view of the alternative needle of FIG. 11.
Figure 11:
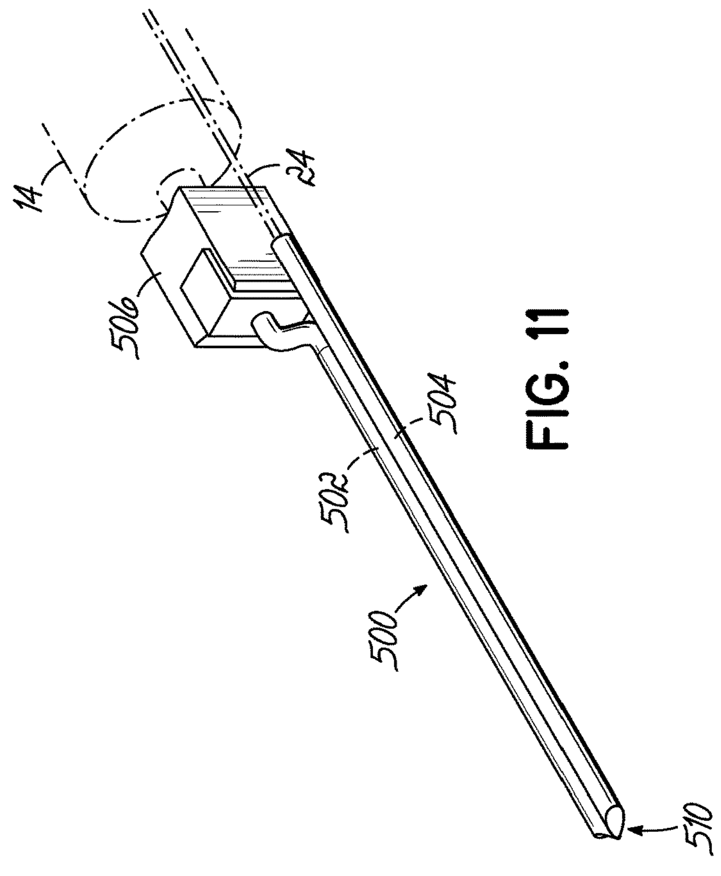
FIG. 11 is a perspective view of an alternative needle for the wire and catheter placement device of an embodiment of the invention.
Figure 13:
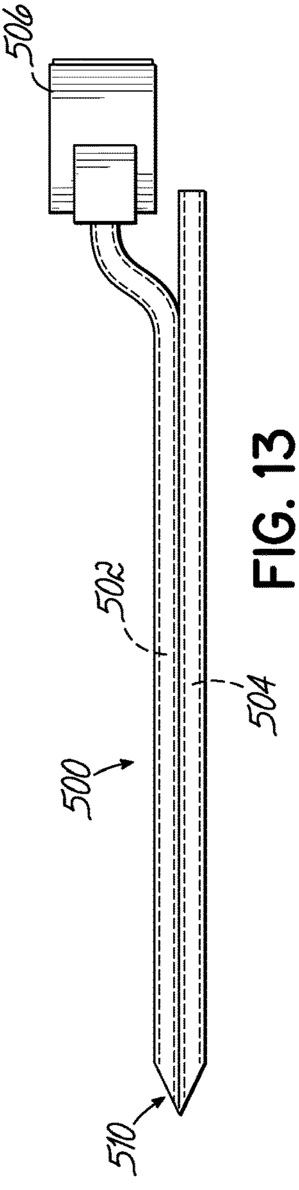
FIG. 13 is a top view of the alternative needle of FIG. 11.

Referring to FIG. 6G, once the needle and wire have entered workspace 84 through tissue 82, such as through an entry point 83, the needle may be withdrawn as shown by arrow 85 and only the wire 24 left in position within the workspace 84. However, the needle mount 150 and needle 132 must be broken apart to allow the advancement of catheter 100 and dilator 102 or any other element of the catheter arrangement on wire 24. The catheter arrangement can then progress in the direction of arrow 87 as illustrated in FIG. 6H. To do so, the ends of the needle mount 150 may be grasped and torn apart as illustrated in FIG. 6H. Generally, the needle 132 will be a breakaway or peelable needle that may be split or have at least one side pull off to free wire 24. The needle mount will also be weakened, such as along the score line 151, to be separated as shown in FIG. 6H. The two parts of the needle mount 150*a* and 150*b*, along with the respective halves of the needle 132 may be pulled apart in the direction of arrows 89 as shown in FIG. 6H. If a double barrel needle is used, as shown in FIGS. 11-13, one side of the needle might be peeled off. Then the needle and mount are removed. The dilator 102 and catheter 100 may be slid along wire 24 into workspace 84, such as through the same tissue entry point 83 that the needle created. Referring to FIG. 6I, the dilator 102 and catheter 100 are shown in position along wire 24 within the workspace 84. Once the catheter 100 is properly positioned, the wire 26 and dilator 102 may be withdrawn as illustrated in FIG. 6J and then the catheter 100 and any respective ports 104 are in position and may be utilized for the desirable medical procedure.

Figure 7:
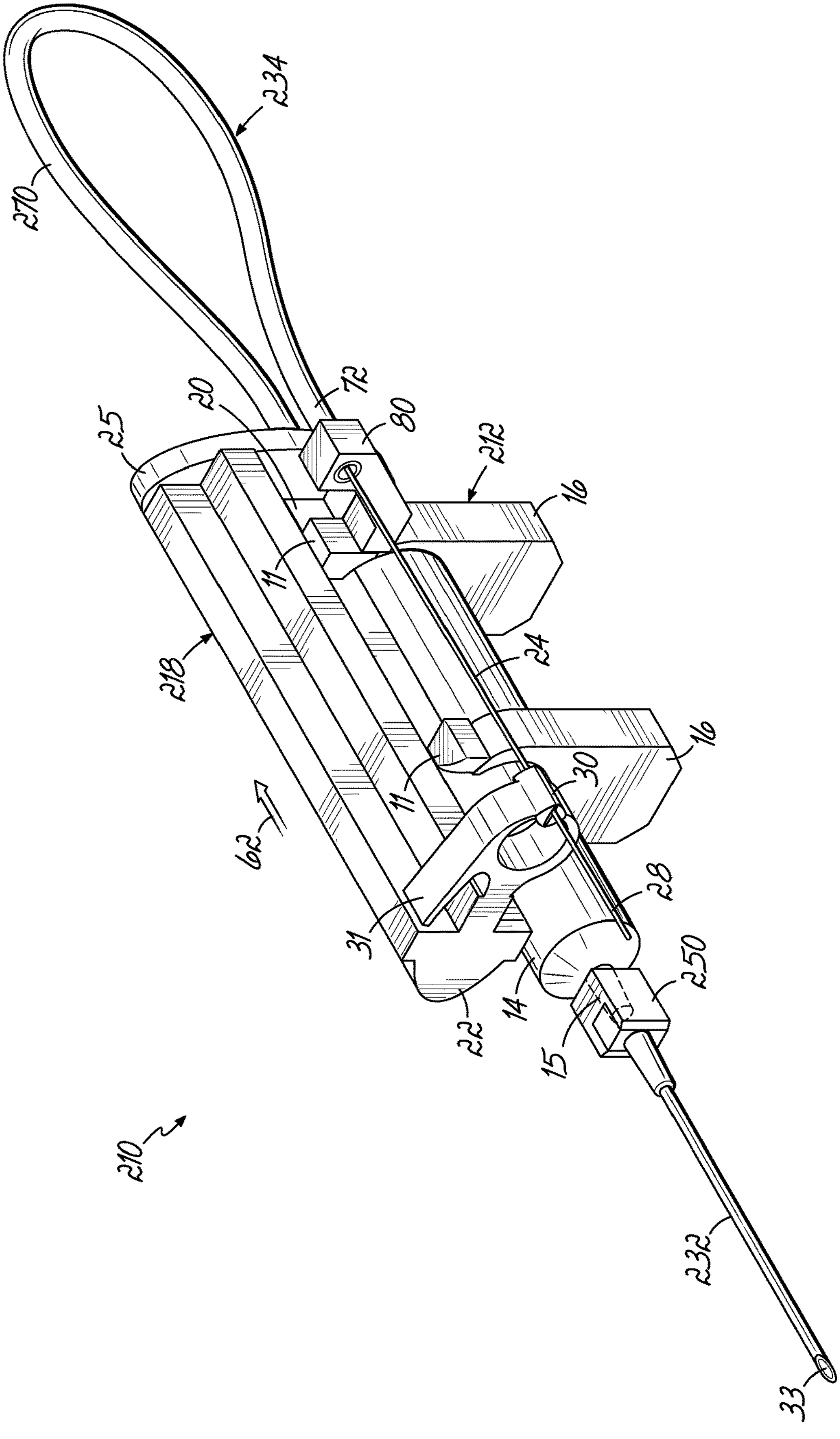
FIG. 7 is a perspective view of wire and catheter placement device in accordance with another embodiment of the invention.
Figure 8A:
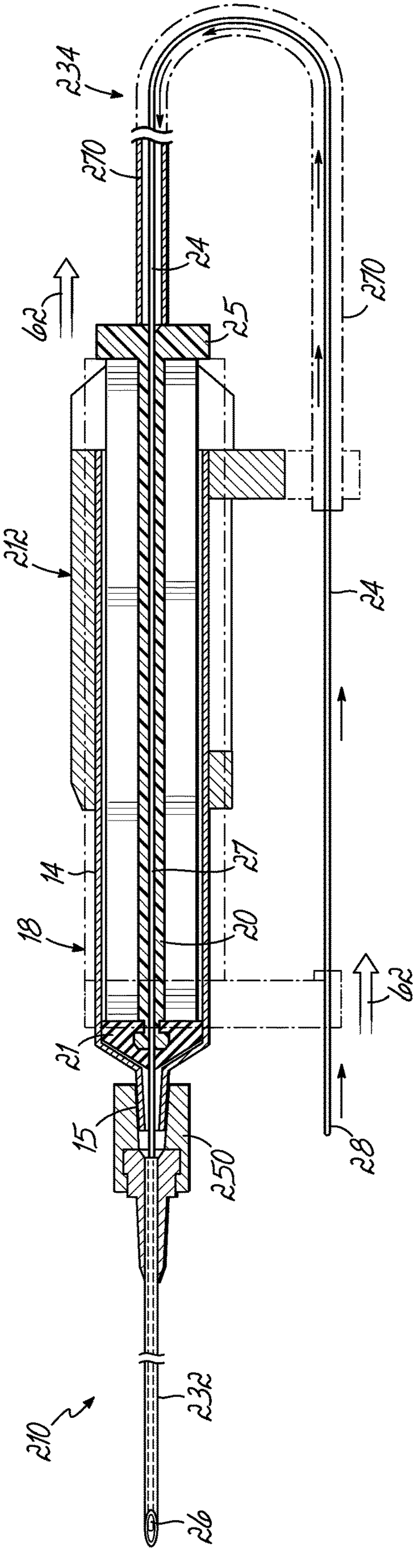
FIG. 8A is a top view, in partial cross-section, of the wire and catheter placement device of FIG. 7, in a forward position, in accordance with an embodiment of the invention.
Figure 8B:
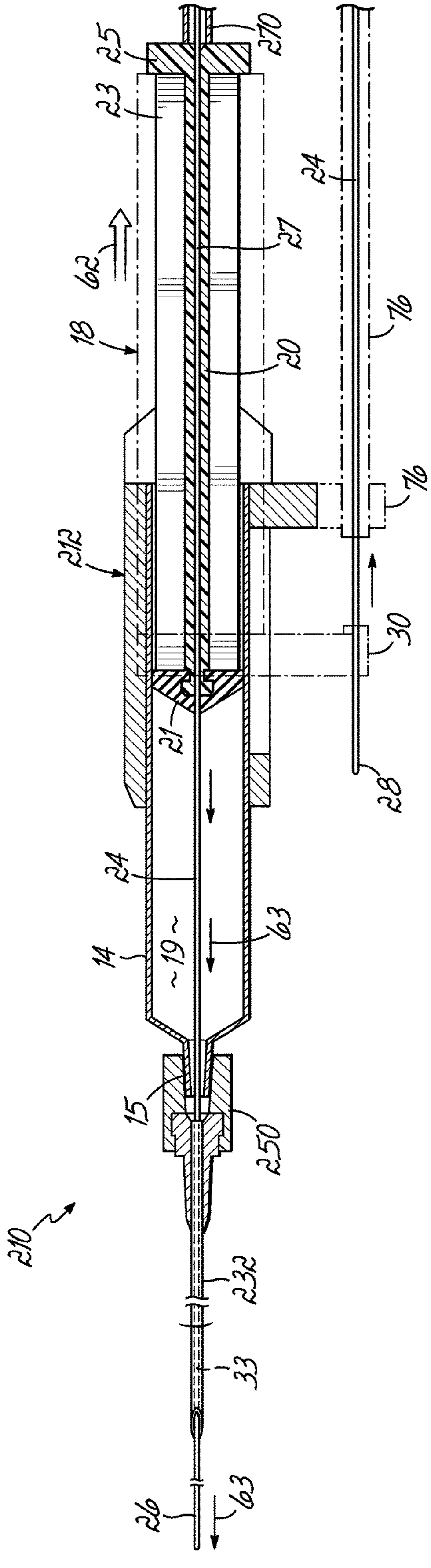
FIG. 8B is a top view, in partial cross-section, of the wire and catheter placement device of FIG. 7, in a retracted position, in accordance with an embodiment of the invention.

One advantage of the preloaded catheter arrangement in FIG. 5 is that a stop structure 13 might be placed on a back end or distal end of the wire. Such a stop structure 13 may prevent the catheter arrangement from falling off a back of the wire or may prevent the back end of the wire from getting pulled past the skin. Since the needle and mount break or peel away, thus removing the need to slide the needle off of the wire, the stop structure may be implemented. Other embodiments of the invention may utilize wire advancing mechanisms that are positioned and operate differently, as well as alternative syringe bodies and needles and needle mounts for advancing the wire 26 in the opposite direction from the movement of the plunger. Specifically, referring to FIGS. 7-8B, an alternative device 210 is implemented that has a housing 212, grip portions 16, a slide 218, and wire gripping structure 30 for the movement of a syringe plunger and wire simultaneously. However, in the embodiment of the device 210 illustrated in FIGS. 7-8B, the wire advancing mechanism 234 is configured to present the wire distal end 24 to proceed through the end 25 of the slide 18 and through plunger 20. As illustrated in FIG. 8A, the plunger 20 may include an internal passage 27 through which wire 24 may progress. As illustrated, the loop guide 270 of the wire advancing mechanism 234 may terminate at the end 25 of the slide which coincides with the end of the plunger and the wire may be guided through the syringe plunger 20 and the syringe body 14 to engage with the needle mount 250 and the needle 232 as the slide 18 and plunger are moved in the direction of arrow 62. As illustrated in FIG. 8A, the wire 24 and particularly the distal end 28 of the wire moves with slide 18 and its direction is changed by the wire advancing mechanism 234 to proceed through the syringe plunger 20, syringe body 14 and through the needle 232 into the appropriate workspace as illustrated in FIG. 8B. That is, as the slide and plunger move in the direction of arrow 62, the wire moves in the direction of arrow 63 through the needle 232 as discussed herein with various of the embodiments.

Figure 9:
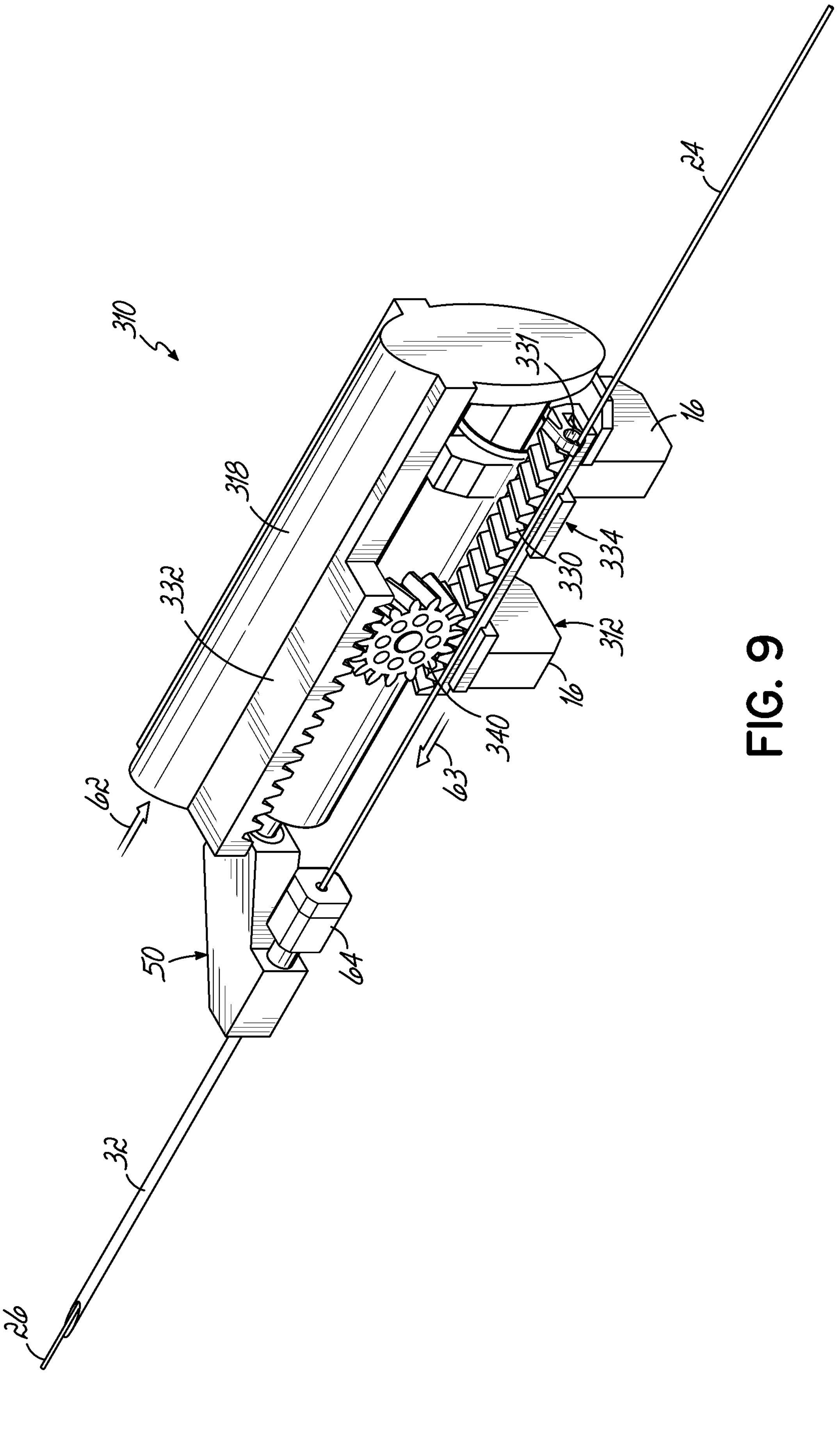
FIG. 9 is a perspective view of wire and catheter placement device in accordance with another embodiment of the invention.
Figure 10:
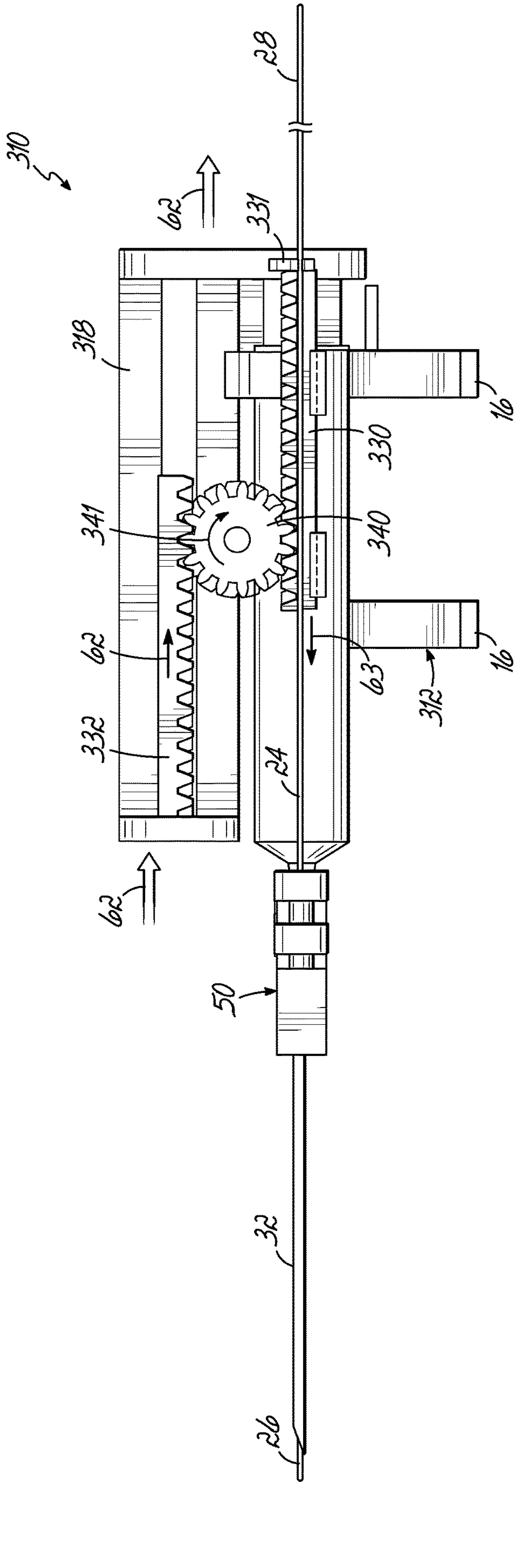
FIG. 10 is a side view of the wire and catheter placement device of, in a forward position.

In accordance with an alternative embodiment of the invention, different wire advancing mechanisms may be utilized. FIGS. 1 and 5 illustrate one version having a loop guide. FIGS. 9 and 10 illustrate an alternative version which is configured for actively advancing the proximal end of the wire forwardly into a needle of the device when the slide moves the syringe plunger from the forward position to a retracted position. In the embodiment of the device 310 as illustrated in FIGS. 9 and 10, the advancing mechanism is an active mechanism, rather than the passive mechanism as with loop guide 70. Specifically, the housing 312 is configured to include a movable rack gear 330. The slide 318 is configured to include an opposing rack gear 332. The rack gear 330 is configured to translate along housing 312 in the direction of arrow 63 when the slide 318 and rack gear 332 are moved to a retracted position in the direction of arrows 62 as shown in FIG. 10. A pinion gear 340 is rotatably mounted with respect to the housing 312 between the two rack gears 330, 332. The pinion gear rotates in the direction of arrow 341 as the rack gear 332 on the slide 318 is translated during movement of the slide and plunger. In turn, the pinion gear 340 acts on the movable rack gear 330 that is translated in the direction of arrow 63. The movable rack gear 330 includes a wire gripping structure 331 which grasps the distal end 28 of the wire 24. As the slide 318 and plunger are moved to a retracted position, the movable rack gear 330 and wire gripping structure 331 are translated in the direction of arrow 63 and thereby translates the wire 24 through needle mount 50 and needle 32 in accordance with features of the invention. Therefore, the wire advancing mechanism 334 as illustrated in FIGS. 9 and 10 shows an embodiment that incorporates active forward movement of the wire upon retracting the plunger, rather than a passive change of direction. As such, the wire advancing mechanism as illustrated and described herein may actively move the wire, rather than passively reverse its direction from the direction of the slide and plunger. One additional use of the active or geared version of a wire advancing mechanism is that the rack gears and pinion gears might be adjusted and configured to increase the feedback to a user such that hand movement in moving the slide and plunger to the retracted position might be adjusted in both the speed of the wire movement (increased or decreased) in the workspace and the force feedback of the wire movement (increased or decreased) to the user's hand. The current use of the passive wire advancing mechanism might provide a 1:1 ratio of hand force and wire movement force. The active wire advancing mechanism as shown in FIGS. 9-10 might provide a higher or lower ratio of forces based on gearing, for example.

FIGS. 11-13 illustrate an alternative embodiment of a needle mount and needle in accordance with an aspect of the invention. The needle mounts 50 and 150 as illustrated in FIGS. 1 and 5, for example, incorporate a sealing mechanism 64 for providing a seal with respect to the movable wire 24 so that negative pressure may be drawn through the needle mount of the syringe body 14 and plunger 20 through the bore of the needle as the wire moves through the same bore. Alternatively, a needle with multiple passages may be implemented such that the passage used to draw the negative pressure is different than the passage which advances the wire. Referring to FIGS. 11-13, a double needle is illustrated for that purpose. Specifically, the double needle 500 incorporates a needle portion or passage 502 for drawing the negative pressure or vacuum utilizing syringe body 14. A separate needle portion or passage 504 receives wire 24 for advancement upon moving a slide/plunger to the retracted position in accordance with the invention. To that end, the needle mount 506 is configured such that negative pressure may be drawn through needle passage 502 while the wire 24 simultaneously advances through needle passage 504. To that end, the passages 502, 504 are generally parallel and share a common pointed tip 510 for penetration into tissue and a workspace. Needle mount 506 incorporates an appropriate aperture 512 for coupling with the tip of the syringe body 14 for initially drawing a negative pressure and then subsequently releasing the slide/plunger upon the proper placement of the needle to move the plunger to a retracted position and move the wire 24 forwardly into the needle.

FIG. 14 illustrates another alternative embodiment of a needle mount and needle arrangement for a device of the invention. The needle mount 650 mounts the needle 32 to be inline with the syringe rather than inline with the advancing wire. To that end, the vacuum passage 654 is straight and feeds into the tip 15 of the syringe. The wire guide passage 652 is arced or otherwise angled to simultaneously feed the advancing wire into needle 32 in accordance with the invention.

While the present invention may be used for placing a wire as a guide wire for placing central venous catheters, it may be used for other purposes and techniques as well. For example, it may be used to place pigtail chest tubes, pigtailed drains for fluid collection, for thoracentesis and paracentesis and for other uses where a Seldinger technique is employed or where a wire or catheter is placed in a body. It may also be used for, but not limited to, placement of wires for angiography, central venous line placement, arterial line placement, image guided percutaneous gastrostomy tube placement, small bore chest tube placement, insertion of pacemaker leads, insertion of central venous pressure monitors, cardiac ablation procedures, percutaneous drain placement, PICC placement, insertion of implantable cardioverter-defibrillators, REBOA (resuscitative balloon occlusion of the aorta), endovascular dialysis fistula creation, and other endovascular procedures (EVAR, TEVAR, TAVR, thromboembolectomy, endovascular stent placement, thrombolysis), for example. The wire placed may be used as a guide wire to guide other elements into position or the wire may be the element left in the workspace for the medical procedure.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A device for interfacing with a syringe body and syringe plunger for delivering a wire into a tissue workspace, the device comprising:

a needle configured for coupling with the syringe body and having at least one bore for guiding a proximal end of the wire into the workspace;

a housing configured for coupling with the syringe body and including at least one portion for engagement by a user;

a slide configured for coupling with the syringe plunger for moving together and in a same direction with the syringe plunger between a forward position and a retracted position, the slide including at least one portion for engagement by the user;

the slide including a wire holding structure for releasably holding a distal end of the wire for moving the distal end and advancing the proximal end of the wire forwardly in the needle when the slide moves together with the syringe plunger from the forward position to the retracted position;

a wire advancing mechanism configured for translating the movement of the wire distal end by the wire holding structure for advancing the proximal end of the wire forwardly in the needle when the wire holding structure and the syringe plunger move together from the forward position to the retracted position.

2. The device of claim 1 wherein the wire holding structure of the slide includes a wire gripping structure for releasably gripping the distal end of the wire for moving the distal end of the wire with the syringe plunger.

3. The device of claim 1 wherein the wire advancing mechanism includes a loop guide for reversing the direction of the wire movement and translating the movement of the wire distal end for advancing the wire proximal end.

4. The device of claim 3 wherein the loop guide has a distal end positioned to receive the wire from the wire holding structure of the slide and a proximal end for guiding the proximal end of the wire into the needle.

5. The device of claim 1 further comprising a needle mount, the needle mount including a guide passage coupled with the at least one needle bore for directing movement of the wire in the needle and a vacuum passage for coupling with the syringe body to create a negative pressure in the at least one needle bore when the syringe plunger moves to the retracted position.

6. The device of claim 5 wherein the guide passage is airtight.

7. The device of claim 5 wherein the guide passage is positioned in-line with the needle for movement of the wire in the needle.

8. The device of claim 5 wherein the needle includes two passages, a first of the needle passages being coupled with the guide passage and a second of the needle passages being coupled with the vacuum passage.

9. A device for interfacing with a syringe body and syringe plunger for delivering a catheter into a tissue workspace, the device comprising:

a wire;

a catheter threaded onto the wire;

a needle configured for coupling with the syringe body and having at least one bore for guiding a proximal end of the wire into the tissue workspace;

a housing configured for coupling with the syringe body and including at least one portion for engagement by a user, the housing releasably securing the catheter;

a slide configured for coupling with the syringe plunger for moving together and in a same direction with the syringe plunger between a forward position and a retracted position, the slide including at least one portion for engagement by the user;

the slide including a wire holding structure for releasably holding a distal end of the wire for moving the distal end and advancing the proximal end of the wire forwardly into the tissue workspace through the catheter and needle when the slide moves together with the syringe plunger from the forward position to the retracted position;

a wire advancing mechanism configured for translating the movement of the wire distal end for advancing the proximal end of the wire forwardly in the catheter and needle when the wire holding structure and the syringe plunger move together from the forward position to the retracted position the catheter configured for being released from the housing and slid along the wire into the tissue workspace.

10. The device of claim 9 wherein the wire holding structure of the slide includes a wire gripping structure for releasably gripping the distal end of the wire for moving the distal end of the wire with the syringe plunger.

11. The device of claim 9 wherein the wire advancing mechanism includes a loop guide for reversing the direction of the wire movement and translating the movement of the wire distal end for advancing the wire proximal end.

12. The device of claim 11 further comprising a dilator threaded onto the wire with the catheter.

13. The device of claim 9 further comprising a needle mount, the needle mount including a guide passage coupled with the at least one needle bore for directing movement of the wire in the needle and a vacuum passage for coupling with the syringe body to create a negative pressure in the at least one needle bore when the syringe plunger moves to the retracted position.

14. The device of claim 13 wherein the needle and needle mount may be broken away from the wire for the catheter to slide along the wire into the workspace.

15. The device of claim 13 wherein the guide passage is positioned in-line with the needle for movement of the wire in the needle.

16. The device of claim 13 wherein the needle includes two passages, a first of the needle passages being coupled with the guide passage and a second of the needle passages being coupled with the vacuum passage.

17. The device of claim 9 wherein the wire advancing mechanism has an output end positioned rearwardly of the catheter so the wire can exit the output end of the wire advancing mechanism and enter the catheter.

* * * * *